United States Patent
Lei et al.

(10) Patent No.: US 11,540,985 B2
(45) Date of Patent: Jan. 3, 2023

(54) STABLE MICROCAPSULE COMPOSITIONS

(71) Applicant: International Flavors & Fragrances Inc., New York, NY (US)

(72) Inventors: Yabin Lei, Holmdel, NJ (US); Li Xu, Edison, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 16/312,307

(22) PCT Filed: Jul. 3, 2017

(86) PCT No.: PCT/US2017/040594
§ 371 (c)(1),
(2) Date: Dec. 21, 2018

(87) PCT Pub. No.: WO2018/006089
PCT Pub. Date: Jan. 4, 2018

(65) Prior Publication Data
US 2019/0231658 A1 Aug. 1, 2019

Related U.S. Application Data

(60) Provisional application No. 62/357,523, filed on Jul. 1, 2016.

(51) Int. Cl.
| | | |
|---|---|---|
| *A61K 8/11* | (2006.01) |
| *A61K 8/26* | (2006.01) |
| *A61Q 15/00* | (2006.01) |
| *A61Q 19/10* | (2006.01) |
| *A61Q 5/00* | (2006.01) |
| *A61K 8/41* | (2006.01) |
| *A61Q 19/00* | (2006.01) |
| *A61K 8/43* | (2006.01) |
| *A61K 8/46* | (2006.01) |
| *A61K 8/73* | (2006.01) |
| *A61K 8/81* | (2006.01) |
| *A61K 8/84* | (2006.01) |
| *A61Q 11/00* | (2006.01) |

(52) U.S. Cl.
CPC ................. *A61K 8/11* (2013.01); *A61K 8/26* (2013.01); *A61K 8/41* (2013.01); *A61K 8/416* (2013.01); *A61K 8/43* (2013.01); *A61K 8/466* (2013.01); *A61K 8/731* (2013.01); *A61K 8/736* (2013.01); *A61K 8/817* (2013.01); *A61K 8/84* (2013.01); *A61Q 5/00* (2013.01); *A61Q 15/00* (2013.01); *A61Q 19/00* (2013.01); *A61Q 19/10* (2013.01); *A61K 2800/10* (2013.01); *A61K 2800/412* (2013.01); *A61K 2800/52* (2013.01); *A61K 2800/5426* (2013.01); *A61K 2800/56* (2013.01); *A61K 2800/654* (2013.01); *A61Q 11/00* (2013.01)

(58) Field of Classification Search
CPC ... A61K 8/11; A61K 8/26; A61K 8/41; A61K 8/416; A61K 8/43; A61K 8/466; A61K 8/731; A61K 8/736; A61K 8/817; A61K 8/84; A61K 2800/10; A61K 2800/412; A61K 2800/52; A61K 2800/5426; A61K 2800/56; A61K 2800/654; A61Q 5/00; A61Q 15/00; A61Q 19/00; A61Q 19/10; A61Q 11/00
See application file for complete search history.

(56) References Cited

U.S. PATENT DOCUMENTS

| | | | |
|---|---|---|---|
| 7,001,592 B1 * | 2/2006 | Traynor | .................... A61K 8/37 424/59 |
| 2008/0317795 A1 * | 12/2008 | Traynor | ................. A61Q 19/10 424/401 |
| 2011/0097369 A1 | 4/2011 | Sunder | |
| 2013/0230574 A1 * | 9/2013 | Struillou | .................. B01J 13/16 424/401 |
| 2013/0337023 A1 | 12/2013 | Lei | |
| 2014/0044760 A1 * | 2/2014 | Lei | ........................... B01J 13/18 424/401 |
| 2014/0287008 A1 | 6/2014 | Lei | |

FOREIGN PATENT DOCUMENTS

| | | |
|---|---|---|
| WO | 2014011860 A2 | 1/2014 |
| WO | 2015023961 A1 | 2/2015 |

OTHER PUBLICATIONS

International Preliminary Report on Patentability in PCT/US2017/040594 dated Jan. 1, 2019.
International Search Report and Written Opinion in PCT/US2017/040594 dated Oct. 19, 2017.

\* cited by examiner

*Primary Examiner* — Ali Soroush
(74) *Attorney, Agent, or Firm* — Licata & Tyrrell P.C.

(57) ABSTRACT

Disclosed are stable microcapsule compositions each containing a microcapsule dispersed in an aqueous phase and a stabilizing agent. The microcapsule compositions are stable for at least 4 weeks when storing at 45° C., and the microcapsule composition is considered stable when (i) the composition has a viscosity of 3000 cP or less and (ii) 20% or less water by volume of the composition is separated from the composition. Also disclosed are consumer products having such a stable microcapsule composition.

17 Claims, No Drawings

STABLE MICROCAPSULE COMPOSITIONS

CROSS REFERENCE TO RELATED APPLICATION

This application is a national stage entry under 35 USC 371 for International Application No. PCT/US2017/040594, filed Jul. 3, 2017, which claims priority to U.S. Application No. 62/357,523, filed Jul. 1, 2016. The contents of both applications are incorporated herein by reference in their entirety.

BACKGROUND

Microcapsules are useful in a variety of applications where there is a need to deliver, apply, or release a fragrance or other active material in a time-delayed and controlled manner.

Conventional microcapsule compositions contain microcapsules dispersed in an aqueous phase. They tend to form gel, separate into layers, release the active material prematurely, etc. See US 2014/0287008 and WO 2015/023961. Certain microcapsule compositions have been developed to improve the stability via engineering a more robust microcapsule wall. See US 20140044760, WO2014011860, and US20130337023. However, these microcapsule compositions still face stability issues including short storage lifetime, gel formation during transportation in a harsh temperature, and instability in consumer products.

There is a need to develop a stable microcapsule composition that can be stored for a extended period of time and provide a long shelf life in consumer products.

SUMMARY

This invention is based on the discovery that a combination of a negatively charged clay and a cationic polymer can stabilize microcapsule compositions.

Accordingly, one aspect of this invention relates to a stable microcapsule composition having a microcapsule dispersed in an aqueous phase and a stabilizing agent, in which the microcapsule composition is stable for at least 4 weeks when storing at 45° C. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition.

Another aspect of this invention relates to a stable microcapsule composition comprising a microcapsule dispersed in an aqueous phase and a stabilizing agent, wherein stabilizing agent is a combination of a negatively charged clay and a cationic polymer. This composition is stable, e.g., for at least 4 weeks when stored at 45° C.

In one embodiment, the microcapsule is present at a level of 10 to 70% (e.g., 20 to 70% and 30 to 60%) by weight of the stable microcapsule compositions described above.

In another embodiment, the negatively charged clay is present at a level of 0.05 to 2% (e.g., 0.05 to 1%, 0.1 to 0.5%, and 0.1 to 0.3%); and the cationic polymer is present at a level of 0.05 to 5% (e.g., 0.05 to 2.5%, 0.1 to 2%, 0.1 to 1%, and 0.2 to 0.7%). An exemplary negatively charged clay is a montmorillonite clay. Suitable cationic polymers are cationic polyquaternium polymers such as a hydroxyethyl cellulose dimethyl diallylammonium chloride copolymer (PQ-4), a copolymer of acrylamide and diallyldimethylammonium chloride (PQ-7), a terpolymer of acrylic acid, methacrylamide-propyl trimethylammonium chloride, and methyl acrylate (PQ-47), and combinations thereof.

Suitable microcapsules of this invention include, but are not limited to, core-shell microcapsules each having a microcapsule wall and a microcapsule core encapsulated by the microcapsule wall. The microcapsule wall can be formed of an encapsulating polymer selected from the group consisting of a polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), and combinations thereof. The microcapsule core can contain an active material selected from the group consisting of a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, and combinations thereof.

Any of the microcapsule compositions described above can further comprise an alkylnaphthalenesulfonate formaldehyde condensate, polyvinylpyrrolidone, polyvinyl alcohol, polystyrene sulfonate, carboxymethyl cellulose, sodium salt of naphthalene sulfonate condensate, copolymer of vinyl pyrrolidone and quaternized dimethylaminoethyl methacrylate, or a combination thereof. When the encapsulating polymer is a polyurea or polyurethane, the polyurea can be a reaction product of a polyfunctional isocyanate and a polyfunctional amine, optionally in the presence of an alkylnaphthalenesulfonate formaldehyde condensate and polyvinylpyrrolidone, and the polyurethane can be a reaction product of a polyfunctional isocyanate and a polyfunctional alcohol as a cross-linking agent, optionally in the presence of an alkylnaphthalenesulfonate formaldehyde condensate and polyvinylpyrrolidone. Each of the alkylnaphthalenesulfonate formaldehyde condensate and polyvinylpyrrolidone, independently, can be present at a level of 0.1 to 5% by weight of the microcapsule composition, and the ratio between the alkylnaphthalenesulfonate formaldehyde condensate and polyvinylpyrrolidone can be 10:1 to 1:10.

In some embodiments, the polyfunctional isocyanate is an aromatic polyfunctional isocyanate, aliphatic polyfunctional isocyanate, or combination thereof, in which the aromatic polyfunctional isocyanate contains a phenyl, tolyl, xylyl, naphthyl, or diphenyl moiety, or two or more of the moieties, and the aliphatic polyfunctional isocyanate is a trimer of hexamethylene diisocyanate, a trimer of isophorone diisocyanate, a biuret of hexamethylene diisocyanate, or a combination thereof. Exemplary aromatic polyfunctional isocyanates are a polymeric methylene diphenyl diisocyanate, a polyisocyanurate of toluene diisocyanate, a trimethylol propane-adduct of toluene diisocyanate, a trimethylol propane-adduct of xylylene diisocyanate, or a combination thereof. Suitable aliphatic polyfunctional isocyanates include those selected from the group consisting of dimers, biurets, symmetric trimers, asymmetric trimers of hexamethylene diisocyanate, and combinations thereof.

In other embodiments, the polyfunctional amine is hexamethylene diamine, hexaethylenediamine, ethylenediamine, 1,3-diaminopropane, 1,4-diamino-butane, diethylenetriamine, pentaethylenehexamine, 1,6-diaminohexane, hydrazine, 1,4-diaminocyclohexane, 1,3-diamino-l-methyl-propane, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, or a combination thereof.

In still other embodiments, the encapsulating polymer is a polyurea that is a reaction product of a polyfunctional isocyanate and a polyfunctional amine, in which the polyisocyanate contains a trimethylol propane-adduct of toluene diisocyanate or a trimethylol propane-adduct of xylylene diisocyanate, and the polyfunctional amine is diethylenetriamine, bis(3-aminopropyl)amine, bis(hexanethylene)triamine, tris(2-aminoethyl)amine, triethylenetetramine, N,N'-bis(3-aminopropyl)-1,3-propanediamine, tetraethylenepentamine, pentaethylenehexamine, branched polyethylenimine, chitosan, nisin, gelatin, 1,3-diaminoguanidine monohydrochloride, 1,1-dimethylbiguanide hydrochloride, or guanidine carbonate, or mixture thereof. These microcapsule compositions can further comprise a polyvinyl alcohol, polystyrene sulfonate, carboxymethyl cellulose, polyvinylpyrrolidone, sodium salt of naphthalene sulfonate condensate, copolymer of vinyl pyrrolidone and quaternized dimethylaminoethyl methacrylate, or combination thereof.

Any one of the microcapsule compositions described above optionally includes a deposition aid selected from the group consisting of polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, and combinations thereof. It can further contain one or more free fragrances or one or more additional microcapsules.

The microcapsule compositions described above typically have a pH value of 2-10 (e.g., 3-9, 4-8, 5-8, and 6-7.5). The pH value can be adjusted by adding an acid or base.

Any of the microcapsule compositions can be in a solid form, e.g., by spray drying.

Also within the scope of the invention is a consumer product containing one or more of the microcapsule compositions described above. Exemplary consumer products include a shampoo, a hair conditioner, a hair rinse, a hair refresher, a hair fixative or styling aid, a hair bleach, a hair dye or colorant, a soap, a body wash, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, an tooth whitener, a denture adhesive, a chewing gum, a breath freshener, an orally dissolvable strips, a chewable candy, a hard candy, a hand sanitizer, an anti-inflammatory balm, an anti-inflammatory ointment, an anti-inflammatory spray, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrib, a foot cream, a facial tissue, a cleansing wipe, a fabric care product, a fabric softener, a fabric refresher, an ironing water, a liquid laundry detergent, a liquid dish detergent, an automatic dish detergent, a unit dose tablet or capsule, a scent booster, a drier sheet, a fine fragrance, a solid perfume, a powder foundation, a liquid foundation, an eye shadow, a lipstick or lip balm, an Eau De Toilette product, a deodorant, a rug deodorizer, a candle, a room deodorizer, a disinfectant, an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, a spray deodorant, a baked product, a bread, a dry biscuit, a cake, a cookie, a chip, a popcorn, a pretzel, an extruded snack, a breakfast cereal, a mueli bar, a precooked finished rice product, an alcoholic or non-alcoholic beverage, a spice blend, a soup, a sauce, a stew, a frozen entrée, a yogurt, an ice cream, a bean curd, a cheese, a soya protein product, a meat product, an egg product, a mayonnaise, a remoulade, a dressing, a seasoning preparation, a fruit preparation, or a vegetable preparation.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The terms "capsule" and "microcapsule" herein are used interchangeably.

The terms "g," "mg," and "μg" refer to "gram," "milligram," and "microgram," respectively. The terms "L" and "mL" refer to "liter" and "milliliter," respectively.

The details of one or more embodiments of the invention are set forth in the description below. Other features, objects, and advantages of the invention will be apparent from the description and the claims.

DETAILED DESCRIPTION

It has been found that a negatively charged clay and a cationic polymer in combination can unexpectedly stabilize microcapsule compositions.

The microcapsule composition of this invention find their utility in a wide range of consumer applications, e.g., personal care products including shampoos, hair conditioners, hair rinses, hair refreshers; personal wash such as bar soaps, body wash, personal cleaners and sanitizers, hydroalcoholic formulations; fabric care such as fabric refreshers, softeners and dryer sheets, ironing water, industrial cleaners, liquid and powder detergent including unit dose capsules, rinse conditioners, and scent booster products; fine fragrances; an Eau De Toilette products; deodorants; roll-on products, and aerosol products.

The microcapsule composition contains a microcapsule dispersed in an aqueous phase in the presence of a stabilizing agent. The microcapsule composition can be stable for at least 4 weeks (e.g., at least 6 weeks, at least 8 weeks, 4 weeks to two years, 4 week to one year, and 4 to 26 weeks) when storing at 45° C.

The stability is measure by both the viscosity and water separation. Known microcapsule compositions tend to form into gels, making them unsuitable for use in consumer products. When turning into a gel, the viscosity of the composition increases to 3000 centipoise (cP) or even 6000 cP. The microcapsule is considered stable if it does not gel out and has a viscosity of 3000 cP or less.

Another measurement of stability is the degree of the separation of water from the microcapsule. Initially, the microcapsule composition is emulsion-like dispersion (i.e., a colloidal suspension) in which the microcapsules are evenly dispersed in the water phase. Over a period of storage, the microcapsules can flocculate and water can separate out from the composition. Such separation will require additional process to turn the composition to a homogenous suspension, during which undesirable microcapsule bursting and fragrance leakage increase. The microcapsule composition is deemed stable if 20% or less water by volume of the composition is separated from the composition.

The components of the microcapsule composition are described in detail below.

Clays

Any clay can be used in this invention. The term "clay" refers to a hydrous layered silicate of the phyllosilicate family, i.e., a silicate sheet based on a two-dimensional structure, in which the basic building blocks are the Si(O, OH) tetrahedral sheets and $M(O,OH)_6$ (M being $Al^{3+}$, $Mg^{2+}$, $Fe^{3+}$, or $Fe^{2+}$) octahedral sheets. See Vaccari, Catalysis Today 1998, 41, 53-71. The Clay can be dioctahedral or trioctahedral, based on the number of octahedral sites per unit cell occupied, which in turn depends essentially on the cation M (e.g., $Al^{3+}$, $Mg^{2+}$, $Fe^{3+}$, or $Fe^{2+}$) present in the octahedral sheets.

Negatively charged clays are particularly useful in this invention. These clays contain fine particles having a net negative electrostatic charge on at least one surface of their sheets. The surface charge is usually balanced by the presence of charge balancing ions (sometimes called exchangeable ions, e.g., sodium and calcium) which are usually present between the layers of the clay and at the edges of the layers.

Preferred negatively charged clays are 2:1 phyllosilicates, in which the clay layers comprise two tetrahedral sheets sandwiching one octahedral sheet. Examples are smectite clays having the general formula $Al_2(Si_2O_5)_2(OH)_2 \cdot nH_2O$ or $Mg_3(Si_2O_5)_2(OH)_2 \cdot nH_2O$, and derivatives thereof, for example in which a proportion of the aluminum ions are replaced with magnesium ions or a proportion of the magnesium ions are replaced with lithium ions and/or some of the hydroxyl ions are replaced by fluoride ions; the derivatives may comprise a further metal ion to balance the overall charge.

The term smectite clays herein include both the clays in which aluminum oxide is present in a silicate lattice and the clays in which magnesium oxide is present in a silicate lattice. Typical smectite clay compounds include the dioctahedral minerals montmorillonite, beidellite, volchonskoites, and nontronite, and the trioctahedral minerals hectorite, saponite, and sauconite, particularly those having an alkali or alkaline earth metal ion within the crystal lattice structure. Preferred smectite clays are montmorillonite clays.

The montmorillonite clays typically have the general formula $HAlSi_2O_6$ but with variable Al—Si ratios, variable amounts of water and usually containing variable amounts of exchangeable cations. These clays can have alkali and alkaline earth metal cations as exchangeable ions. Examples include sodium and calcium montmorillonites. Another exemplary montmorillonite clay is an aluminous member of the group accorded the empirical Formula $(OH)_4Si_8$ $(Al_{3.34}Mg_{0.66}Na_{0.66})O_{20}$. Both bentonite and hectorite are also members of the montmorillonite clays.

Commercially available montmorillonite clays include GELWHITE series (highly purified montmorillonite clays) marketed as GELWHITE-GP, GELWHITE-H, and GELWHITE-L by BYK Additives & Instruments, Germany. Other commercial products include Mineral Colloid BP, Mineral Colloid MO, Gelwhite MAS 100 (sc), Gelwhite MAS 101, Gelwhite MAS 102, Gelwhite MAS 103, Bentolite WH, Bentolite L10, Bentolite H, Bentolite L, Permont SX10A, Permont SC20, and Permont HN24 (Southern Clay Products, Texas, USA); Bentone EW and Bentone MA (Dow Corning); Bentonite USP BL 670 and Bentolite H4430 (Whitaker, Clarke & Daniels); Clarit 100 G1 and Clarit 1100 G1 (calcium bentonites from Süd Chemie AG); and Volclay 2 (sodium bentonite from Süd Chemie AG).

Examples of synthetic hectorites useful in the present invention include those products sold under the trade names Laponite RD, Laponite RDS, Laponite XLG, Laponite XLS, Laponite D, Laponite DF, Laponite DS, Laponite S and Laponite JS (all from Southern Clay products, Texas, USA, a subsidiary of Rockwood).

Additional suitable smectite clays are disclosed in U.S. Pat. Nos. 3,862,058, 3,948,790, 3,954,632 and 4,062,647, and in EP-A-299,575, EP-A-313,146, and EP0352878B1.

Clays may be used as obtained from the supplier and may contain conventional additives such as, for example, disintegrating agents (also known as peptisers) and water of hydration. The clays may be used in their natural state or in a purified or semi-purified form, for example with the removal of mineral impurities.

The cation exchange capacity (CEC) of a clay is a well-known parameter and may be determined by well-established analytical techniques, including by electrodialysis, by exchange with ammonium ion followed by titration or by a methylene blue procedure, all as fully described in Grimshaw, "The Chemistry and Physics of Clays", pp. 264-265, Interscience (1971). It is customary to measure the cation exchange capacity of a clay in terms of milliequivalents per 100 g of dry clay (meq/100 g).

Preferred clays for use in the present invention have a cation exchange capacity of from 0.7 meq/100 g to 150 meq/100 g (e.g., 30 meq/100 g to 100 meq/100 g).

The clays preferably have a volume-based median particle diameter (D0.5) from 0.001 µm to 80 µm (e.g., 0.01 µm to 50 µm, 0.02 µm to 20 µm, and 0.05 to 5 µm). Particle diameters can be determined using a Malvern Mastersizer (Malvern Instruments, UK).

The permanent charges of the silicate layers in the clay particles result from isomorphous substitutions. However, the degree of substitution changes from layer to layer within certain limits so that the interlayer cation density also varies from interlayer space to interlayer space and may also vary in directions parallel to the layers (heterogeneous charge distribution). The distribution of the interlayer cation density can easily be determined by the alkylammonium method as described in Mermut and Lagaly, Clays and Clay Minerals 49 (2001), 393-397. The average layer charge of montmorilonite clays varies between 0.2 and 0.4 eq/formula unit (Si, Al)$_4$O$_{10}$. Some montmorillonite clays have an average layer charges around 0.3 eq/formula unit. The surface charge can be in the range of 0.01 to 2 Coulomb/m$^2$ ("Cm$^{-2}$") (e.g., 0.02 to 1 Cm$^{-2}$ and 0.05 to 0.5 Cm$^{-2}$).

The level of the clay in the total composition is preferably from 0.01 to 10 wt % of the total composition (e.g., 0.05 to 2 wt %, 0.05 to 1%, 0.1 to 0.5%, and 0.1 to 0.3%).

In the compositions of the invention, the clay is advantageously present in the form of a dispersion (for example a sol or gel) or as a suspension.

Cationic Polymers

Suitable cationic polymers are cationic polyquaternium (hereinafter "PQ") polymers such as those listed in Table 1 below.

TABLE 1

| PQ | Description | Trade Name |
|---|---|---|
| 1 | Ethanol, 2,2',2"-nitrilotris-, polymer with 1,4-dichloro-2-butene and N,N,N',N'-tetramethyl-2-butene-1,4-diamine | Polyquad (Alcon) |
| 2 | Poly[bis(2-chloroethyl) ether-alt-1,3-bis[3-(dimethylamino)propyl]urea] | Mirapol A-15 |
| 4 | Hydroxyethyl cellulose dimethyl diallylammonium chloride copolymer; Diallyldimethylammonium chloride-hydroxyethyl cellulose copolymer | Celquat L-200, H-100, L-200 |
| 5 | Copolymer of acrylamide and quaternized dimethylammoniumethyl methacrylate | Merquat 5, RETEN (Hercules) |
| 6 | Poly(diallyldimethylammonium chloride) | Merquat 100, 106, Mirapol 100 |
| 7 | Copolymer of acrylamide and diallyldimethylammonium chloride | Merquat 550, 550L, 550PR, S, 7SPR, 740, 2200, Mirapol 550, Polyquart 770/NA, Conditioneze 7 |
| 8 | Methyl and Stearyl Dimethylaminoethyl Methacrylate Quaternized with Dimethyl Sulfate | |
| 9 | Polydimethylaminoethyl Methacrylate Quaternized with Methyl Bromide | |
| 10 | Quaternized hydroxyethyl cellulose | Merquat 10, Celquat SC-230M, SC-240C, SC-140C, Ucare Polymer |
| 11 | copolymer of vinylpyrrolidone and quaternized dimethylaminoethyl methacrylate | Luviquat PQ 11PN, Gafquat 775N, 440, 734, 775 |
| 14 | Ethanaminium, N,N,N-Trimethyl-2-[(2-Methyl-1-Oxo-2-Propenyl)Oxy]-, Methyl Sulfate, Homopolymer | |
| 15 | Ethanaminium, N,N,N-Trimethyl-2-[(2-Methyl-1-Oxo-2-Propenyl)Oxy]-, Chloride, Polymer with 2-Propenamide | Rohagit KF 720F (Rohm GmbH) |
| 16 | Copolymer of vinylpyrrolidone and quaternized vinylimidazole | Luviquat FC 370, HM 552, Style, FC 550, Excellence |
| 17 | Poly(Oxy-1,2-Ethanediyl(Dimethyliminio)-1,3-Propanediylimino(1,6-Dioxo-1,6-Hexanediyl)Imino-1,3-Propanediyl(Dimethyliminio)-1,2-Ethanediyl Dichloride | Mirapol AD |
| 18 | Poly[oxy-1,2-ethanediyl(dimethyliminio)-1,3-propanediylimino-(1,6-dioxo-1,6-heptanediyl)imino-1,3-propanediyl(dimethyliminio)-1,2-ethanediyl dichloride] | Luviquat 500 |
| 19 | Ethenol, polymer with aminomethyloxirane | Arlatone PQ-220 (ICI Americas) |
| 20 | Ethenyl octadecyl ether, polymer with aminomethyloxirane | Arlatone PQ-225 |
| 24 | Cellulose, 2-[2-Hydroxy-3-(Trimethylammonio)Propoxy]Ethyl Ether, Chloride (Similar to PQ-10) | Quatrisoft Polymer LM-200 (Dow Chemical) |
| 27 | Hexanediamide, N,N'-bis(3-(Dimethylamino)Propyl)-, Polymer with N,N'-bis(3-Dimethylamino)Propyl Urea and 1,1'-Oxybis(2-Chloroethane), Block | |
| 28 | Copolymer of vinylpyrrolidone and methacrylamidopropyl trimethylammonium | Gafquat HS-100, Conditioneze NT-10 |
| 29 | Chitosan, 2,3-Dihydroxypropyl-2-Hydroxy-3-(Trimethylammonio)Propyl Ether, Chloride | Quaternized Chitosan |
| 30 | Ethanaminium, NCarboxymethyl)-N,N-Dimethyl-2-((2-Methyl-1-Oxo-2-Propenyl)Oxy)-, Inner Salt, Polymer with Methyl 2-Methyl-2-Propenoate | Mexomere PX (Chimex) |
| 31 | 2-Propenenitrile, Homopolymer, Hydrolyzed, Block, Reaction Products with N,N-Dimethyl-1,3-Propanediamine, Di-Et Sulfate-Quaternized | Hypan QT100 (Lipo) |
| 32 | Poly(acrylamide 2-methacryloxyethyltrimethyl ammonium chloride) (Similar to PQ-15) | Cosmedia CTC (Cognis GmbH) - PQ-32 + other, Salcare SC92 (Ciba Corp.) PQ-32 + other |

TABLE 1-continued

| PQ | Description | Trade Name |
|---|---|---|
| 33 | Ethanaminium, N,N,N-Trimethyl-2-[1-Oxo-2-Propenyl)Oxy]-, Chloride, Polymer with 2-Propenamide | Lanoquat DES-50, Ultimer CG-200 (Nalco), Sepigel Quat33 (Seppic) - PQ-33 + other |
| 34 | Poly(diethyliminio-1,3-propanediyldimethyliminio-1,3-propanediyl dibromide) | Mexomere PAK (Chimex) |
| 35 | Ethanaminium, N-carboxymethyl-N,N-dimethyl-2-(2-methyl-1-oxo-2-propenyloxy)-, inner salt, polymer with N,N,N-trimethyl-2-(2-methyl-1-oxo-2-propenyloxy)ethanaminium methyl sulfate | Plex 3074 L (Rohm GmbH) |
| 37 | N,N,N-Trimethyl-2-[(Methyl-1-Oxo-2-Propenyl)Oxy]Ethanaminium Chloride, Homopolymer | Ultragel 300 (Cognis), Synthalen CN, CR, CU (3V Group), Syntran PC 5320 (Interpolymer) |
| 42 | Poly[oxyethylene(dimethyliminio)ethylene(dimethylimino)ethylene dichloride] | Busan 1507 (Buckman Labs) |
| 44 | Poly(2-oxopyrrolidin-1-ylethylene, 3-methylimidazolium-1-ylethylene methyl sulfate) | Luviquat Ultracare, MS 370 (BASF), Softenol PQ44 (Zdchimmer & Schwarz Italianat S.p.A) |
| 45 | Glycine, N-methyl-N-[2-[(2-methyl-1-oxo-2-propenyl)oxy]ethyl]-, polymer with 2-(dimethylamino)ethyl 2-methyl-2-propenoate, compound with dimethyl sulfate | Plex 3073L (Rohm GmbH) |
| 46 | 1H-Imidazolium, 1-Ethenyl-3-Methyl-, Methyl Sulfate, Polymer with 1-Ethenylhexahydro-2H-Azepin-2-one and 1-Ethenyl-2-Pyrrolildinone | Luviquat Hold |
| 47 | 1-Propanaminium, N,N,NTrimethyl-3-((2-Methyl-1-Oxo-2-Propenyl)Amino)-, Chloride, Polymer with Methyl 2-Propenoate and 2-Propenoic Acid | Merquat 2001, 2001N |
| 48 | Polymeric quaternary ammonium salt of formed from methacryloyl ethyl betaine, 2-hydroxyethyl methacrylate and methacryloyl ethyl trimethyl ammonium chloride | Plascize L-450 (Goo Chemical) |
| 49 | polymeric quaternary ammonium salt formed by the reaction of methacryloyl ethyl betaine, PEG-9 methacrylate and methacryloyl ethyl trimethyl ammonium chloride | Plascize L-440 (Goo Chemical) |
| 50 | Carboxylatoethyldimethylammonioethyl 2-methyl-2-propenoate homopolymer | Plascize L-401 (Goo Chemical) |
| 55 | 1-Dodecanaminium, N,NDimethyl-N-[3-[(2-Methyl-1-Oxo-2-Propenyl)-AminoPropyl]-, Chloride, Polymer with N-[3-(Dimethylamino)Propyl]-2-Methyl-2-Propenamide and 1-Ethenyl-2-Pyrrolidinone | Styreze W |
| 56 | 5-Isocyanato-1-(isocyanatomethyl)-1,3,3-trimethylcyclohexane, polymer with 1,3-butanediol and bis(2-hydroxyethyl)dimethylammonium methyl sulfate | Hairrol UC-4 (Sanyo Chemical) |
| 57 | 12-Hydroxy-9(Z)octadecenamidopropyltrimethylammonium chloride, polymers with ricinus communis (castor) oil, isooctdecanoic acid and butandioic acid | Zenigloss Q (Zenitech) |
| 59 | Poly(20,25-dioxo-2,5,10,15,18-pentamethyl-10-(2-hydroxy-3-(3-phenyl-2-propenamido)propyldimethylammonio) propyl)-10-azonia-1,4,7,13,16,19-hexaoxapentacosanediyl) chloride | Crodasorb UV-HPP (Croda, Inc.) - PQ-59 and Butylene Glycol |
| 60 | 9-Octadecenoic Acid, 12-Hydroxy-, [(2-Hydroxyethyl)-Imino]Di-2,1-Ethanediyl Ester, Polymer with 5-Isocyanato-1-(Isocyanatomethyl)-1,3,3-Trimethylcyclohexane, Compd. with Diethyl Sulfate | Polylipid PPI-RC (Alzo/Bernel) - PQ-60 and Propylene Glycol |
| 61 | 2-Methyl-2-propenoyloxyethyl N,N,N-trimethylammonioethyl phosphate inner salt, polymer with octadecyl 2-methyl-2-propenoate | Lipidure-S (NOF) |
| 62 | Polymeric quaternary ammonium salt of butyl methacrylate, polyethylene glycol methyl ether methacrylate, ethylene glycol dimethacrylate and 2-methacryloylethyl trimonium chloride with 2,2'-azobis(2-methyl propionamidine)dihydrochloride | Nanoaquasome (Amore Pacific/Kyung-do) |
| 64 | 2-Methyl-2-propenoyloxyethyl N,N,N-trimethylammonio-ethyl phosphate inner salt, polymer with 2-hydroxy-3-(2-methyl-2-propenoyl)oxypropyltrimethylammonium chloride | Lipidure-C (NOF) |
| 67 | 2-Hydroxyethyl cellulose ether, reaction products with N,N,N-trimethyl-N-oxiranylmethylammonium chloride and N-dodecyl-N,N-dimethyl-N-oxiranylmethylammonium chloride | Softcat (Dow Chemical) |
| 68 | 1-Ethenyl-2-pyrrolidinone, polymer with 1-ethenylimidazole and 1-ethenyl-3-methylimidazolium methyl sulfate | Luviquat Supreme |
| 69 | polymeric quaternary ammonium salt composed of vinyl caprolactam, vinylpyrrolidone, dimethylaminopropyl methacrylamide (DMAPA), and methacryloylaminopropyl lauryldimonium chloride | Aquastyle 100, 300 (ISP) |
| 71 | | ColaMoist 300P (Colonial Chemical Inc) |
| 72 | polymeric quaternary ammonium salt of hydroxethylcellulose reacted with a coco-alkyl dimethyl ammonium substituted epoxide | Mirustyle CP (Croda) |

TABLE 1-continued

| PQ | Description | Trade Name |
|---|---|---|
| 73 | polymeric quaternary ammonium salt consisting of propyltrimonium chloride acrylamide, ethyltrimonium chloride methacrylate and dimethylacrylamide monomers; Propanaminium, N,N,N-trimethyl-3-(2-propenamido)-, chloride, polymer with N,N,N-trimethyl-2-(2-methyl-2-propenoyloxy)ethanaminium chloride and N,N-dimethyl-2-propenamide | Diaformer C-802, C-823 (Mitsubishi Chem), Diasleek C-802, C-823 (Mitsubishi Chem) |
| 74 | | Mirapol PB 20 (Rhodia) Polycare Boost (Rhodia) |
| 75 | O-(2-Hydroxy-2-trimethylammoniopropyl)starch chloride, reaction products with O-(3-dodecyldimethylammonio-2-hydroxypropyl)starch chloride | Amylomer Cat 220EMU (Grafe Chemie) |
| 77 | Cocoglucoside Crosspolymer Hydroxypropyltrimonium Chloride | Colonial Poly SugaQuat TM-8610P (Colonial Chemical Inc) |
| 78 | Decylglucoside Crosspolymer Hydroxypropyl Laurdimonium Chloride | Colonial Poly SugaQuat L-1010P (Colonial Chemical Inc) |
| 79 | Decylglucoside Crosspolymer Hydroxypropyl Steardimonium Chloride | Colonial Poly SugaQuat S-1010P (Colonial Chemical Inc) |
| 80 | Laurylglucoside Crosspolymer Hydroxypropyl Laurdimonium Chloride | Colonial Poly SugaQuat L-1210P (Colonial Chemical Inc) |
| 81 | Laurylglucoside Crosspolymer Hydroxypropyl Steardimonium Chloride | Colonial Poly SugaQuat S-1210P (Colonial Chemical Inc) |
| 82 | Laurylglucoside Crosspolymer Hydroxypropyltrimonium Chloride | Colonial Poly SugaQuat TM-1218P (Colonial Chemical Inc) |
| 84 | polymeric quaternary ammonium salt of acrylamidopropyltrimethylammonium chloride, trimethylaminoethyl methacrylate, dimethylacrylamide and hydroxyethylmethacrylate | Diasleek C-824 (Mitsubishi Chemical) |
| 85 | polymeric quaternary ammonium salt of acrylamidopropyltrimethylammonium chloride, dimethylacrylamide and hydroxyethylmethacrylate | Diasleek C-825 (Mitsubishi Chemical) |
| 87 | polymeric quaternary ammonium salt of vinylpyrrolidone, vinylimidazole and diallyldimethyl ammonium chloride | Luviquat Sensation (BASF) |
| 88 | Poly(Dilinoleyldimonium hydroxypropyl)chlorides) | ColaQuat PDQ (Colonial Chemical Inc) |
| 90 | polymeric quaternary ammonium salt of acrylamide and hydroxyethylcellulose quaternized with diallyldimethyl ammonium chloride | Hymoquat AK325R (Hymo Corporation) |
| 91 | polymeric quaternary ammonium salt of hydroxypropyl methacrylate and polyethylene glycol methacrylate quaternized with ethyltrimonium chloride methacrylate | Syntran 5500 (Interpolymer) - PQ-91 and PA |
| 92 | GLYCERYLAMIDOETHYL METHACRYLATE/STEARYL METHACRYLATE COPOLYMER | Ceracute-G (NOF) |
| 101 | | Deposilk Q1 (Air Products) |

Preferred cationic polymers include a hydroxylethyl cellulose dimethyl diallylammonium chloride copolymer (PQ-4), a copolymer of acrylamide and diallyldimethylammonium chloride (PQ-7), a terpolymer of acrylic acid, methacrylamidopropyl trimethylammonium chloride, and methyl acrylate (PQ-47), and combinations thereof.

Microcapsules

Microcapsules can be prepared following encapsulation procedures known in the art. See for example U.S. Pat. Nos. 2,800,457, 3,870,542, 3,516,941, 3,415,758, 3,041,288, 5,112,688, 6,329,057, and 6,261,483.

One class of microcapsules contains a microcapsule wall encapsulating a microcapsule core wherein the microcapsule wall is formed of an encapsulating polymer and the microcapsule core contains an active material. Another type of microcapsules are the so-called reloadable microcapsules wherein the microcapsule core contains a sacrifice solvent and is free of an active material.

Wall forming materials (i.e., encapsulating polymers) include a melamine formaldehyde, polyurethane, polysiloxanes, polyurea, polyamide, polyimide, polyvinyl alcohol, polyanhydride, polyolefin, polysulfone, polysaccharide, protein, polypeptide, polylactide (PLA), polyglycolide (PGA), polyorthoester, polyphosphazene, silicone, lipid, modified cellulose, gum, polystyrene, polyester, polyether, and combination of these materials. Other polymeric materials that are functional are ethylene maleic anhydride copolymer, styrene maleic anhydride copolymer, ethylene vinyl acetate copolymer, and lactide glycolide copolymer. Biopolymers that are derived from alginate, chitosan, collagen, dextran, gelatin, and starch can also be used as the encapsulating materials. Additionally, capsules can be made via the simple or complex coacervation of gelatin. Preferred encapsulating wall polymers include those formed from isocyanates, acrylates, acrylamide, acrylate-co-acrylamide, hydrogel monomers, sol-gel precursors, gelatin, melamine-formaldehyde or urea-formaldehyde condensates, as well as similar types of aminoplasts.

Certain specific encapsulating polymers are described below as non-limiting examples.

1.1 Polyurea/Polyurethane Capsules

Polyurea capsules each have a microcapsule wall formed of an encapsulating polymer that is the polymerization reaction product of a polyisocyanate and a polyamine/ polyalcohol. See WO 2004/054362; EP 0 148149; EP 0 017 409 B1; U.S. Pat. Nos. 4,417,916, 4,124,526, 4,285,720, 4,681,806, 5,583,090, 6,340,653 6,566,306, 6,730,635, 8,299,011, WO 90/08468, and WO 92/13450. In addition, the encapsulating polymer can also be prepared using a carbonyl crosslinker and a polyamine/polyalcohol.

1.1.1 Polyisocyanates

The polyisocyanates each contain two or more isocyanate (—NCO) groups. Suitable polyisocyanates include, for example, 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

Other suitable commercially-available polyisocyanates include LUPRANATE M20 (PMDI, commercially available from BASF containing isocyanate group "NCO" 31.5 wt %), where the average n is 0.7; PAPI 27 (PMDI commercially available from Dow Chemical having an average molecular weight of 340 and containing NCO 31.4 wt %) where the average n is 0.7; MONDUR MR (PMDI containing NCO at 31 wt % or greater, commercially available from Bayer) where the average n is 0.8; MONDUR MR Light (PMDI containing NCO 31.8 wt %, commercially available from Bayer) where the average n is 0.8; MONDUR 489 (PMDI commercially available from Bayer containing NCO 30-31.4 wt %) where the average n is 1.0; poly[(phenylisocyanate)-co-formaldehyde] (Aldrich Chemical, Milwaukee, Wis.), other isocyanate monomers such as DESMODUR N3200 (poly(hexamethylene diisocyanate) commercially available from Bayer), and TAKENATE D110-N (xylene diisocyanate adduct polymer commercially available from Mitsui Chemicals corporation, Rye Brook, N.Y., containing NCO 11.5 wt %), DESMODUR L75 (a polyisocyanate base on toluene diisocyanate commercially available from Bayer), and DESMODUR IL (another polyisocyanate based on toluene diisocyanate commercially available from Bayer).

In some embodiments, the polyisocyanate used in the preparation of the capsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the polyurea/polyureathane polymers as capsule wall materials.

The average molecular weight of certain suitable polyisocyanates varies from 250 to 1000 Da and preferable from 275 to 500 Da. In general, the range of the polyisocyanate concentration varies from 0.1% to 10%, preferably from 0.1% to 8%, more preferably from 0.2 to 5%, and even more preferably from 1.5% to 3.5%, all based on the weight of the capsule delivery system.

More examples of suitable polyisocyanates can be found in WO 2004/054362; WO 2015/023961; EP 0 148149; EP 0 017 409 B1; U.S. Pat. Nos. 4,417,916, 4,124,526, 5,583,090, 6,566,306, 6,730,635, PCT 90/08468, PCT WO 92/13450, U.S. Pat. Nos. 4,681,806, 4,285,720 and 6,340,653.

1.1.2 Carbonyl Crosslinker

The carbonyl crosslinkers each have at least two functional groups, e.g., a first functional group and a second functional group.

The first functional group is an electrophilic group reactive towards the polyfunctional amine or the polyfunctional alcohol to form a network of the encapsulating polymer. Examples include formyl, keto, carboxyl, a carboxylate ester group, an acyl halide group, an amide group, a carboxylic anhydride group, an alkyl halide group, an epoxide group, an aziridine group, an oxetane group, an azetidine group, a sulfonyl halide group, a chlorophosphate group, an isocyanate group, an $\alpha,\beta$-unsaturated carbonyl group, an $\alpha,\beta$-unsaturated nitrile group, or an $\alpha,\beta$-unsaturated methanesulfonyl group. Preferably, the first function group is a carbonyl electrophilic group containing a carbonyl group such as formyl, keto, carboxyl, a carboxylate ester group, an acyl halide group, an amide group, a carboxylic anhydride group, an $\alpha,\beta$-unsaturated carbonyl group, a trifluoromethanesulfonate group, and a p-toluenesulfonate group.

The second functional group is an electrophilic group reactive towards the polyfunctional amine or the polyfunctional alcohol. It can be selected from the groups listed immediately above.

Examples of a carbonyl crosslinker include glutaric dialdehyde, succinic dialdehyde, and glyoxal; as well as compounds such as glyoxyl trimer and paraformaldehyde, bis (dimethyl) acetal, bis(diethyl) acetal, polymeric dialdehydes, such as oxidized starch. Preferably the crosslinking agent is a low molecular weight, difunctional aldehyde, such as glyoxal, 1,3-propane dialdehyde, 1,4-butane dialdehyde, 1,5-pentane dialdehyde, or 1,6-hexane.

1.1.3 Polyfunctional Amines

Suitable polyfunctional amines include those described in WO 2015/023961. Examples are hexamethylenediamine, hexaethylenediamine, ethylenediamine, 1,3-diaminopropane, 1,4-diamino-butane, diethylenetriamine, pentaethylenehexamine, bis(3-aminopropyl)amine, bis(hexanethylene) triamine, tris(2-aminoethyl)amine, triethylene-tetramine, N,N'-bis(3-aminopropyl)-1,3-propanediamine, tetraethylenepentamine, amino-2-methyl-1-propanol, chitosan, 1,3-diamino-guanidine, 1,1-dimethylbiguanide, guanidine, arginine, lysine, histidine, ornithine, nisin, gelatin, and combinations thereof.

Other suitable polyamines include polyethylenimine and branched polyethylenimine ("BPEI"). Representative BPEI structure is shown below:

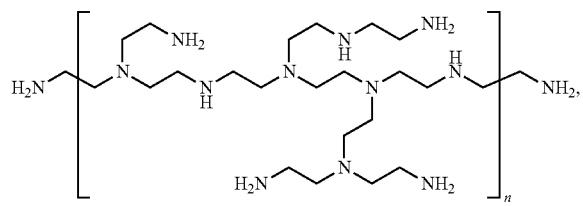

in which n is an integer from 1 to 20,000 (e.g., 1 to 10,000, 2 to 5,000, and 2 to 1,000). BPEI for use in this invention preferably has a molecular weight of 500 to 5,000,000 Daltons (e.g., 500 to 1,000,000 Daltons, 750 to 500,000 Daltons, 750 to 100,000 Daltons, 750 to 50,000 Daltons, 10,000 to 50,000).

BPEI are commercially available from Sigma-Aldrich (St. Louis, Mo.; average molecular weight 25,000 Daltons) and Polysciences Inc. (Warrington, Pa.; various products having molecular weight of 600, 1200, 1800, 10,000, 70,000, 750,000, 250,000, and 2,000,000 Daltons).

1.1.4 Polyfunctional Alcohols

Suitable polyfunctional alcohols are also described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, and combinations thereof.

1.2 Aminoplast and Gelatin Microcapsules

A representative process used for aminoplast encapsulation is disclosed in US 2007/0078071, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in Application GB 2006709 A; the production of micro-capsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845; amido-aldehyde resin in-situ polymerized capsules (see EP 0 158 449 A1); etherified urea-formaldehyde polymers (see U.S. Pat. No. 5,204,185); melamine-formaldehyde microcapsules as described in U.S. Pat. No. 4,525,520; cross-linked oil-soluble melamine-formaldehyde precondensates as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymers as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine-formaldehyde precondensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing this invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alcohol, e.g., methanol, ethanol, 2-propanol, 3-propanol, 1-butanol, 1-pentanol or 1-hexanol, thereby forming a partial ether where the mole ratio of melamine/urea:formaldehyde:alcohol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846 and 6,261,483, and Lee et al. (2002) J. Microencapsulation 19, 559-569.

Examples of urea-formaldehyde pre-condensates useful in the practice of this invention are URAC 180 and URAC 186, trademarks of Cytec Technology Corp. of Wilmington, Del. Examples of melamine-formaldehyde pre-condensates useful in the practice if this invention, include, but are not limited to, CYMEL U-60, CYMEL U-64 and CYMEL U-65, trademarks of Cytec Technology Corp. of Wilmington, Del. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from about 9:1 to about 1:9, preferably from about 5:1 to about 1:5 and most preferably from about 2:1 to about 1:2.

In one embodiment, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides available from BASF. The molecular weights of these materials can range from 10,000 to 1,000,000 Daltons.

Urea-formaldehyde or melamine-formaldehyde capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkylmalonates, alkyl aceto acetates and polyvinyl alcohol aceto acetates.

1.3 Sol-Gel Microcapsules

Sol-gel microcapsules each have a sol-gel polymer as the encapsulating polymer. The sol-gel polymer is the polymerization product of a sol-gel precursor, a compound capable of forming a sol-gel polymer. The sol-gel precursors are typically those containing silicon, boron, aluminum, titanium, zinc, zirconium, and vanadium. Preferred precursors are organosilicon, organoboron, organoaluminum including metal alkoxides and b-diketonates, and combinations thereof. See U.S. Pat. No. 9,532,933.

1.4 Hydrogel Microcapsules

Hydrogel microcapsules are prepared using a polymerizable material such as a monofunctional or multifunctional acrylic or methacrylic acid, or ester thereof. See e.g., WO2014/011860. Exemplary materials useful for preparing hydrogel microcapsules are listed below.

1.4.1 Monomers

Preferred bi- or polyfunctional vinyl monomers include by way of illustration and not limitation, acrylic acid, methacrylic acid, 2-hydroxyethyl acrylate, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-ethylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1- methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate, triethylene glycol diacrylate, triethylene glycol dimethacrylate, diethylene glycol diacrylate, diethylene glycol dimethacrylate, tripropylene glycol diacrylate, aliphatic or aromatic urethane diacrylates, difunctional urethane acrylates, ethoxylated bisphenol diacrylate, ethoxylated bisphenol dimethylacrylate, ethoxylated aliphatic difunctional urethane methacrylates, ethoxylated trimethylolpropane triacrylate, ethoxylated pentaerythritol tetraacrylate, dipropylene glycol diacrylate, aliphatic or aromatic urethane dimethacrylates, epoxy acrylates, epoxymethacrylates, tetraethylene glycol dimethacrylate, tetraethylene glycol diacrylate, polyethylene glycol dimethacrylate, polyethylene glycol diacrylate, 1,3-butylene glycol diacrylate, 1,3-butylene glycol dimethacrylate, 1,4-butanediol dimethacrylate, 1,4-butaneidiol diacrylate, 1,6-hexanediol diacrylate, 1,6-hexanediol dimethacrylate, neopentyl glycol diacrylate, alkoxylated hexanediol diacrylate, alkoxylated cyclohexane dimethanol diacrylate, propoxylated neopentyl glycol diacrylate, trimethylolpropane trimethacrylate, trimethylolpropane triacrylate, pentaerythritol triacrylate, propoxylated trimethylolpropane triacrylate, propoxylated glyceryl triacrylate, ditrimethyloipropane tetraacrylate, dipentaerythritol pentaacrylate, and the like. Representative ester monomers of methacrylic acid, which can be used include 2-hydrox ethyl methacrylate, glycidyl methacrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, 2-(dimethylamino)ethyl methacrylate, 2-(diethylamino)ethyl methacrylate, 2-(diisopropylamino)ethyl methacrylate, N-(2-aminoethyl)methacrylamide hydrochloride, 2-aminoethyl methacrylate hydrochloride, N-(3-aminopropyl)methacrylamide hydrochloride, 2-(tert-butylamino)ethyl methacrylate, and the like.

The above monomers may be employed separately or in various mixtures. The use of multifunctional acrylate and methacrylate will lead to the formation of cross-linked network polymers upon polymerization. Such polymers have desirable properties such as good mechanical strength, elasticity, toughness, and flexibility. Examples of multifunctional acrylates and methacrylates of use in this invention include, but are not limited to, ethylene glycol dimethacrylate (EGDMA), trimethylolpropane trimethacrylate, trimethyloyl triacrylate, pentaerythritol triacrylate, pentaerythritol tetracrylate, bisphenol A dimethacrylate, di (trimethylolpropane) tetraacrylate (DTTA), 1-(acryloyloxy)-3-(methacryloyloxy)-2-propanol (AOOP), trimethylolpropane ethoxylate triacrylate (TPETA), dipentaerythritol pentaacrylate, hexane diacrylate, poly (ethylene glycol) dimethacrylate (PEGDMA), and 1,6-hexandiol dimethacrylate (HDDMA), 1,4-butandiol dimethacrylate, 1,3-butandiol dimethacrylate, 1,6-hexandiol diacrylate, 1,4-butandiol diacrylate, 1,3-butandiol diacrylate.

In certain embodiments, the acrylic or methacrylic acid, or ester thereof, makes up less than 25% by mass, preferably 5 to 20% by mass, or more preferably 10 to 15% by mass of the oil phase.

1.4.2 Initiators

Initiators are often used to start the polymerization reactions. Examples include but not limited to: AIBN, sodium persulfate, benzoyl peroxide, and ammonium persulfate.

1.5 Coascervate Capsules

Proteins useful in coacervation processes include albumins, vegetable globulins and gelatines. The gelatine may be fish, pork, beef, and/or poultry gelatine, for example. According to a preferred embodiment, the protein is fish, beef or poultry gelatine. According to a more preferred embodiment, the protein is warm water fish gelatine.

Typical non-protein polymers useful in complex coacervation methods include, in particular, negatively charged polymers. For example, they may be selected from gum arabic, xanthan, agar, alginate salts, cellulose derivatives, for example carboxymethyl cellulose, pectinate salts, carrageenan, polyacrylic and methacrylic acid, and/or mixtures thereof. Further suitable non-proteins can be derived from the literature, for example from to WO 2004/022221.

A cross-linking agent is typically used to harden the coating layer. Suitable cross-linking agents include formaldehyde, acetaldehyde, glutaraldehyde, glyoxal, chrome alum, or transglutaminase. Preferably, transglutaminase is used at 10-100, preferably 30-60 activity units per gram of gelatine. This enzyme is well described and commercially obtainable.

1.6 Microcapsule Formation Aids

Most microcapsule formation aids are used as dispersants (namely, emulsifiers or surfactants). They facilitate the formation of stable emulsions containing nano- or micro-sized oil drops to be encapsulated. Further, microcapsule formation aids improve the performance of the microcapsule by stabilizing capsules and/or their deposition to the target areas or releasing to the environment. Performance is measured by the intensity of the fragrance release during the use experience, such as the pre-rub and post-rub phases in a laundry experience. The pre-rub phase is the phase when the microcapsules have been deposited on the cloth, e.g., after a fabric softener containing microcapsules has been used during the wash cycle. The post-rub phase is after the microcapsules have been deposited and the microcapsules are broken by friction or other similar mechanisms.

The amount of these microcapsule formation aids is anywhere from about 0.1 to about 40 percent by weight of the microcapsule, more preferably from 0.1 to about 10 percent, more preferably 0.1 to 5 percent by weight.

Preferred microcapsule formation aids are polyvinyl pyrrolidone, polyvinyl alcohol, poly(styrene sulfonate), carboxymethyl cellulose, sodium salt of naphthalene sulfonate condensate, co-polymer of ethylene and maleic anhydride, an alginate, hyaluronic acid, poly(acrylic acid), carboxymethylcellulose, copolymers of acrylic acid and acrylamide, copolymer of acrylamide and acrylamidopropyltrimonium chloride, terpolymers of (acrylic acid, acrylamide, and acrylamidopropyltrimonium chloride), partially or completely hydrolyzed polyvinyl acetate polymers (i.e., polyvinyl alcohol), and combinations thereof.

Other microcapsule formation aids include water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfosuccinates, dioctyl sulfosuccinate, sodium dilaurylsulfosuccinate, poly(styrene sulfonate) sodium salt, isobutylene-maleic anhydride copolymer, gum arabic, sodium alginate, cellulose sulfate and pectin, isobutylene-maleic anhydride copolymer, gum arabic, carrageenan, sodium alginate, pectic acid, tragacanth gum, almond gum and agar; semi-synthetic polymers such as sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Commercially available surfactants include, but are not limited to, sulfonated naphthalene-formaldehyde condensates such as MORWET D425 (sodium salt of alkylnaphthalenesulfonate formaldehyde condensate, Akzo Nobel, Fort Worth, Tex.); partially hydrolyzed polyvinyl alcohols such as MOWIOLs, e.g., MOWIOL 3-83 (Air Products), Ultalux FP, Ultalux FA, Ultalux AD, Selvol 203 (Sekisui), OKS-8089 (Sourus); ethylene oxide-propylene oxide block copolymers or poloxamers such as PLURONIC, SYNPERONIC or PLURACARE materials (BASF); sulfonated polystyrenes such as FLEXAN II (Akzo Nobel); ethylene-maleic anhydride polymers such as ZEMAC (Vertellus Specialties Inc.); copolymer of acrylamide and acrylamidopropyltrimonium chloride such as Salcare SC 60 (BASF); and Polyquaternium series such as Polyquaternium 11 ("PQ11;" a copolymer of vinyl pyrrolidone and quaternized dimethylaminoethyl methacrylate; sold by BASF as LUVIQUAT PQ11 AT 1). Surfactant MOWIOL 3-83 has a viscosity of 2-4 mPa·S (e.g., 3 mPa·S), a degree of hydrolysis of 80-85% (e.g., 83%), an ester value of 170-210 mg KOH/g (e.g., 190 mg KOH/g), and a residual unhydrolyzed acetyl content of 13-18% (e.g., 15%).

In other embodiments, the capsule formation aid is a processing aid such as hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms; natural gums such as alginate esters, carrageenan, xanthanes, agar-agar, pectines, pectic acid, and natural gums such as gum arabic, gum tragacanth and gum karaya, guar gums and quaternized guar gums; gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), Ultrez 20 (Acrylates/C10-30 Alkyl Acrylate Crosspolymer), Carbopol® Ultrez 30 (cross-linked homopolymer of acrylic acid polymerized in a cyclohexane and ethyl acetate co-solvent system.), Aculyn Excel (Acrylates Copolymer), Carbopol 981 (Carbomer), and the like, and their quaternized forms.

The capsule formation aid may also be used in combination with carboxymethyl cellulose ("CMC"), polyvinylpyrrolidone, polyvinyl alcohol, alkylnaphthalenesulfonate formaldehyde condensates, and/or a surfactant during processing to facilitate capsule formation. Examples of surfactants that can be used in combination with the capsule formation aid include, but are not limited to, cetyl trimethyl ammonium chloride (CTAC), poloxamers such as PLURONICS (e.g., PLURONIC F127), PLURAFAC (e.g., PLURAFAC F127), or MIRANET-N, saponins such as QNATURALE (National Starch Food Innovation); or a gum Arabic such as Seyal or Senegal. In certain embodiments, the CMC polymer has a molecular weight range between about 90,000 Daltons to 1,500,000 Daltons, preferably between about 250,000 Daltons to 750,000 Daltons and more preferably between 400,000 Daltons to 750,000 Daltons. The CMC polymer has a degree of substitution between about 0.1 to about 3, preferably between about 0.65 to about 1.4, and more preferably between about 0.8 to about 1.0. The CMC polymer is present in the capsule slurry at a level from about 0.1% to about 2% and preferably from about 0.3% to about 0.7%. in other embodiments, polyvinylpyrrolidone used in this invention is a water-soluble polymer and has a molecular weight of 1,000 to 10,000,000. Suitable polyvinylpyrrolidone are polyvinylpyrrolidone K12, K15, K17, K25, K30, K60, K90, or a mixture thereof. The amount of polyvinylpyrrolidone is 2-50%, 5-30%, or 10-25% by weight of the capsule delivery system. Commercially available alkylnaphthalenesulfonate formaldehyde condensates include MORWET D-425, which is a sodium salt of naphthalene sulfonate condensate by Akzo Nobel, Fort Worth, Tex.

In food products, food-grade dispersants are use. The term "food-grade dispersant" refers to a dispersant having a quality as fit for human consumption in food. They can be natural or non-natural products. A natural product or surfactant refers to a product that is naturally occurring and comes from a nature source. Natural products/surfactants include their derivatives which can be salted, desalted, deoiled, fractionated, or modified using a natural enzyme or microorganism. On the other hand, a non-natural surfactant is a chemically synthesized surfactant by a chemical process that does not involve an enzymatic modification.

Natural dispersants include quillaja saponin, lecithins, gum arabic, pectin, carrageenan, chitosan, chondroitin sulfate, cellulose gum, modified starch, whey protein, pea protein, egg white protein, silk protein, gelatin of fish, proteins of porcine or bovine origin, ester gum, fatty acids, and combinations thereof.

Non-natural dispersants include N-lauroyl-L-arginine ethyl ester, sorbitan esters, polyethoxylated sorbitan esters, polyglyceryl esters, fatty acid esters, and combination thereof.

Other food safe dispersant can also be included in the microcapsule of this invention. Examples include ammonium phosphatides, acetic acid esters of mono- and diglycerides (Acetem), lactic acid esters of mono- and diglycerides of fatty acids (Lactem), citric acid esters of mono and diglycerides of fatty acids (Citrem), mono and diacetyl tartaric acid esters of mono and diglycerides of fatty acids (Datem), succinic acid esters of monoglycerides of fatty acids (SMG), ethoxylated monoglycerides, sucrose esters of fatty acids, sucroglycerides, polyglycerol polyricinoleate, propane-1,2-diol esters of fatty acids, thermally oxidized soya bean oil interacted with mono- or diglycerides of fatty acids, sodium stearoyl lactylate (SSL), calcium stearoyl lactylate (CSL), stearyl tartrate, polyglycerol esters of interesterified castor oil acid (E476), sodium stearoyllatylate, sodium lauryl sulfate, polyoxyethylated hydrogenated castor oil (for instance, such sold under the trade name CREMOPHOR), block copolymers of ethylene oxide and propylene oxide (for instance as sold under the trade name PLURONIC or the trade name POLOXAMER), polyoxyethylene fatty alcohol ethers, and polyoxyethylene stearic acid ester.

1.7 Additional Wall Polymer

The Encapsulating polymer can also include one or more additional wall polymers, e.g., a second, third, fourth, fifth, or sixth polymer. The additional polymers can be selected from the group consisting of silica, polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof.

1.8 Encapsulation Methods

Conventional encapsulation methods can be used to prepare the microcapsules. See WO 2015/023961.

By way of illustration, to prepare a microcapsule having a polyurea encapsulating polymer, an oil-in-water emulsion is first prepared containing (i) a polyamine, a polyalcohol, or mixture thereof, (ii) a polyisocyanate, carbonyl crosslinker, or mixture thereof, (iii) an oil phase having a hydrophilic core solvent and a hydrophobic core solvent, and (iv) an aqueous phase having a microcapsule formation aid and water. The reaction between the polyamine/polyalcohol and the polyisocyanate/carbonyl crosslinker occurs when the temperature of the reaction mixture is raised or a catalyst (such as a transglutaminase for catalyzing amide formation) is added to the mixture.

Catalysts suitable for use in the polyurea/polyurethane formation are transglutaminases, metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate and dibutyltin dilaurate.

The resultant microcapsule slurry is then cured at a predetermined temperature for a predetermined period of time.

In accordance with some embodiments, the microcapsules prepared according to the methods above are cured at a temperature in the range of, e.g., 15° C. to 230° C. (e.g., 55° C. to 90° C., 55° C. to 75° C., and 90° C. to 130° C.) for 1 minute to 10 hours (e.g., 0.1 hours to 5 hours, 0.2 hours to 4 hours and 0.5 hours to 3 hours). A skilled person in the art can determine, without undue experiments, the curing temperature, duration, and the heating rate.

To obtain microcapsules with more leaching of the active material, certain embodiments of this invention provide for a cure at a low temperature, e.g., less than 100° C. In some embodiments, the cure temperature is at or less than 90° C. In other embodiments, the cure temperature is at or less than 80° C.

In one embodiment, the capsules are heated to a target cure temperature at a linear rate of 0.5 to 2° C. per minute (e.g., 1 to 5° C. per minute, 2 to 8° C. per minute, and 2 to 10° C. per minute) over a period of 1 to 60 minutes (e.g., 1 to 30 minutes). The following heating methods may be used: conduction for example via oil, steam radiation via infrared, and microwave, convection via heated air, steam injection and other methods known by those skilled in the art. The target cure temperature used herein refers to the minimum temperature in degrees Celsius at which the capsules may be cured to retard leaching.

2. Active Materials

The microcapsule compositions of the invention have one or more active materials in the external hydrophilic solvent. Nonlimiting examples include those described in WO 2016/049456. These active material include flavor or fragrance ingredients, taste masking agents, taste sensates, malodor counteracting agents, vitamins, antibacterials, sunscreen actives, antioxidants, anti-inflammatory agents, anesthetics, analgesics, antifungal agents, antibiotics, anti-viral agents, anti-parasitic agents, anti-infectious and anti-acne agents, dermatological active ingredients, enzymes and co-enzymes, skin whitening agents, anti-histamines, chemotherapeutic agents, and insect repellents. In addition to the active materials listed above, the products of this invention can also contain dyes, colorants or pigments, naturally obtained extracts (for example paprika extract and black carrot extract), and aluminum lakes. The microcapsule compositions of the invention are particularly suitable for encapsulating fragrances containing one or more aldehydes, amines, and/or alcohols. Aldehydes/amines/alcohols can react with microcapsule wall forming materials such as polyisocyanates, silicate, acrylates, etc.

In some embodiments, the amount of active material in the microcapsule composition is from 0.1 to 95% (e.g., 1 to 90%, 2% to 80%, 4 to 70%, and 5 to 50%) by weight of the composition. The amount of the capsule wall is from 10 to 98% (e.g., 20 to 95%, 30 to 90%, and 50 to 80%) by weight of the capsule. The amount of the microcapsule core (the sum of the hydrophilic and hydrophobic core solvents) is from 2 to 90% (e.g., 5 to 80%, 10 to 70%, and 20 to 50%) by weight of the capsule.

In some microcapsule compositions, the ratio between the capsule and active material is 4:1 to 40:1 (e.g., 5:1 to 30:1 and 6:1 to 20:1).

3. Adjunct Materials

In addition to the active materials, the present invention also contemplates the incorporation of adjunct materials including solvent, emollients, and core modifier materials in the core encapsulated by the capsule wall. Other adjunct materials are nanoscale solid particulate materials, polymeric core modifiers, solubility modifiers, density modifiers, stabilizers, humectants, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of from 0.01% to 25% (e.g., from 0.5% to 10%) by weight of the capsule.

Suitable examples include those described in WO 2016/049456 and US 2016/0158121.

4. Deposition Aids

A capsule deposition aid from 0.01 to 25% (with a lower limit of 0.01%, 0.1%, 0.2%, 0.5%, 1%, 2%, and 5% and an upper limit of 25%, 20%, 15%, 10%, 8%, 5%, and 3%), more preferably from 5 to 20% can be included by weight of the capsule. The capsule deposition aid can be added during the preparation of the capsules or it can be added after the capsules have been made.

These deposition aids are used to aid in deposition of capsules to surfaces such as fabric, hair or skin. These include anionically, cationically, nonionically, or amphoteric water-soluble polymers. Suitable deposition aids include polyquaternium-4, polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, an acrylamidopropyltrimonium chloride/acrylamide copolymer, a methacrylamidopropyl-trimonium chloride/acrylamide copolymer, and combinations thereof. Other suitable deposition aids include those described in WO 2016049456, pages 13-27. Additional deposition aids are described in US 2013/0330292, US 2013/0337023, and US 2014/0017278.

5. Microcapsule Delivery System Formulations

The microcapsule can be formulated into a capsule delivery system (e.g., a microcapsule composition) for use in consumer products.

The capsule delivery system can be a slurry containing in an external hydrophilic solvent (e.g., water, ethanol, and a combination thereof) the capsule at a level 0.1 to 80% (e.g., 70-75%, 40-55%, 50-90%, 1 to 65%, and 5 to 45%) by weight of the capsule delivery system.

In some embodiments, the capsule and its slurry prepared in accordance with the present invention is subsequently purified. See US 2014/0017287. Purification can be achieved by washing the capsule slurry with water until a neutral pH is achieved.

6. Additional Components

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. The capsule delivery system can also contain one or more (e.g., two, three, four, five or six more) different capsules including different capsules of this invention and other capsules such as such as aminoplasts, hydrogel, sol-gel, polyurea/polyurethane capsules, and melamine formaldehyde capsules. More exemplary delivery systems that can be incorporated are coacervate capsules (see WO 2004/022221) and cyclodextrin delivery systems (see WO 2013/109798 and US 2011/03085560).

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethylammonium ion). A precursor can be ester and another suitable derivative, which, during the process of preparing a polyurea or polyurethane capsule composition of this invention, is capable of converting to the compound, polymer, or agent and being used in preparing the polyurea or polyurethane capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R or S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine include L-ornithine and its salts/hydrates (e.g., monohydrochloride) and D-ornithine and its salts/hydrates (e.g., monohydrochloride).

7. Applications

The delivery systems of the present invention are well-suited for use, without limitation, in the following products:

a) Household products
   i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818
   ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
   iii. Scent Boosters such as those described in U.S. Pat. Nos. 7,867,968, 7,871,976, 8,333,289, US 2007/0269651 A1, and US2014/0107010 A1.
   iv. Fabric Care Products such as Rinse Conditioners (containing 1 to 30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, 4,767,547 and 4,424,134

Liquid fabric softeners/fresheners contains at least one fabric softening agent present, preferably at a concentration of 1 to 30% (e.g., 4 to 20%, 4 to 10%, and 8 to 15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01 to 2.5%, preferably 0.02 to 1.25% and more preferably 0.1 to 0.63%. As another example, when the fabric softening agent is 20% by weight of the fabric softener, the active material is 0.04 to 10%, preferably 0.08 to 5% and more preferably 0.4 to 2.5%. The active material is a fragrance, malodor counteractant or mixture thereof. The liquid fabric softener can have 0.15 to 15% of capsules (e.g., 0.5 to 10%, 0.7 to 5%, and 1 to 3%). When including capsules at these levels, the neat oil equivalent (NOE) in the softener is 0.05 to 5% (e.g., 0.15 to 3.2%, 0.25 to 2%, and 0.3 to 1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

v. Liquid dish detergents such as those described in U.S. Pat. Nos. 6,069,122 and 5,990,065
   vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562
   vii. All-purpose Cleaners including bucket dilutable cleaners and toilet cleaners
   viii. Bathroom Cleaners
   ix. Bath Tissue
   x. Rug Deodorizers
   xi. Candles
   xii. Room Deodorizers
   xiii. Floor Cleaners
   xiv. Disinfectants
   xv. Window Cleaners
   xvi. Garbage bags/trash can liners
   xvii. Air Fresheners including room deodorizer and car deodorizer, scented candles, sprays, scented oil air freshener, Automatic spray air freshener, and neutralizing gel beads
   xviii. Moisture absorber
   xix. Household Devices such as paper towels and disposable Wipes
   xx. Moth balls/traps/cakes b) Baby Care Products
   i. Diaper Rash Cream/Balm
   ii. Baby Powder c) Baby Care Devices
   i. Diapers
   ii. Bibs
   iii. Wipes d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.
   i. Tooth Paste. An exemplary formulation as follows:
      1. calcium phosphate 40-55%
      2. carboxymethyl cellulose 0.8-1.2%
      3. sodium lauryl sulfate 1.5-2.5%
      4. glycerol 20-30%
      5. saccharin 0.1-0.3%
      6. flavor oil 1-2.5%
      7. water q.s. to 100%
         A typical procedure for preparing the formulation includes the steps of (i) mixing by a blender according to the foregoing formulation to provide a toothpaste, and (ii) adding a composition of this invention and blending the resultant mixture till homogeneous.
   ii. Tooth Powder
   iii. Oral Rinse
   iv. Tooth Whiteners
   v. Denture Adhesive
e) Health Care Devices
   i. Dental Floss
   ii. Toothbrushes
   iii. Respirators
   iv. Scented/flavored condoms
f) Feminine Hygiene Products such as Tampons, Feminine Napkins and Wipes, and Pantiliners
g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
   i. Personal Cleansers (bar soaps, body washes, and shower gels)
   ii. In-shower conditioner
   iii. Sunscreen ant tattoo color protection (sprays, lotions, and sticks)
   iv. Insect repellants
   v. Hand Sanitizer
   vi. Antiinflammatory balms, ointments, and sprays
   vii. Antibacterial ointments and creams
   viii. Sensates
   ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deordorant.
   x. Wax-based Deodorant. An exemplary formulation as follows:
      1. Parafin Wax 10-20%
      2. Hydrocarbon Wax 5-10%
      3. White Petrolatum 10-15%
      4. Acetylated Lanolin Alcohol 2-4%
      5. Diisopropyl Adipate 4-8%
      6. Mineral Oil 40-60%
      7. Preservative (as needed)

The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
   xi. Glycol/Soap Type Deodorant. An exemplary formulation as follows:
      1. Propylene Glycol 60-70%
      2. Sodium Stearate 5-10%
      3. Distilled Water 20-30%
      4. 2,4,4-Trichloro-2'- Hydroxy Diphenyl Ether, manufactured by the Ciba-Geigy Chemical Company and a Trademark of the Ciba-Geigy Chemical Company) 0.01-0.5%
         The ingredients are combined and heated to 75° C. with stirring until the sodium stearate has dissolved. The resulting mixture is cooled to 40° C. followed by addition of a composition of this invention.
   xii. Lotion including body lotion, facial lotion, and hand lotion
   xiii. Body powder and foot powder
   xiv. Toiletries
   xv. Body Spray
   xvi. Shave cream and male grooming products
   xvii. Bath Soak
   xviii. Exfoliating Scrub
h) Personal Care Devices
   i. Facial Tissues
   ii. Cleansing wipes
i) Hair Care Products
   i. Shampoos (liquid and dry powder)
   ii. Hair Conditioners (Rinse-out conditioners, leave-in conditioners, and cleansing conditioners)
   iii. Hair Rinses
   iv. Hair Refreshers
   v. Hair perfumes
   vi. Hair straightening products
   vii. Hair styling products, Hair Fixative and styling aids
   viii. Hair combing creams
   ix. Hair wax
   x. Hair foam, hair gel, nonaerosol pump spray
   xi. Hair Bleaches, Dyes and Colorants
   xii. Perming agents
   xiii. Hair wipes
j) Beauty Care
   i. Fine Fragrance—Alcoholic. Compositions and methods for incorporating fragrance capsules into alcoholic fine fragrances are described in U.S. Pat. No. 4,428,869. Alcoholic fine fragrances may contain the following:
      1. Ethanol (1-99%)
      2. Water (0-99%)
      3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0-1%)
      4. Optionally an emulsifier or an emollient may be included including but not limited to those listed above
   ii. Solid Perfume
   iii. Lipstick/lip balm iv. Make-up cleanser
v. Skin care cosmetic such as foundation, pack, sunscreen, skin lotion, milky lotion, skin cream, emollients, skin whitening
vi. Make-up cosmetic including manicure, mascara, eyeliner, eye shadow, liquid foundation, powder foundation, lipstick and cheek rouge k) Consumer goods packaging such as fragranced cartons, fragranced plastic bottles/boxes l) Pet care products
   i. Cat litter
   ii. Flea and tick treatment products
   iii. Pet grooming products
   iv. Pet shampoos
   v. Pet toys, treats, and chewables
   vi. Pet training pads
   vii. Pet carriers and crates m) Confectionaries confectionery, preferably selected from the group consisting of chocolate, chocolate bar products, other products in bar form, fruit gums, hard and soft caramels and chewing gum
   i. Gum
      1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), or vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or 6,986,709.) 20-25%
      2. Powdered sugar 45-50%
      3. glucose 15-17%
      4. starch syrup 10-13%
      5. plasticizer 0.1%
      6. flavor 0.8-1.2%
         The components described above were kneaded by a kneader according to the foregoing formulation to provide a chewing gum. Encapsulated Flavor or sensate is then added and blended till homogeneous.
   ii. Breath Fresheners
   iii. Orally Dissolvable Strips
   iv. Chewable Candy
   v. Hard Candy n) Baked products, preferably selected from the group consisting of bread, dry biscuits, cakes and other cookies;

o) snack foods, preferably selected from the group consisting of baked or fried potato chips or potato dough products, bread dough products and corn or peanut-based extrudates;
   i. Potato, tortilla, vegetable or multigrain chips
   ii. Popcorn
   iii. Pretzels
   iv. Extruded stacks p) Cereal Products preferably selected from the group consisting of breakfast cereals, muesli bars and pre-cooked finished rice products q) Alcoholic and non-alcoholic beverages, preferably selected from the group consisting of coffee, tea, wine, beverages containing wine, beer, beverages containing beer, liqueurs, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
   i. Ready to drink liquid drinks
   ii. Liquid Drink Concentrates
   iii. Powder Drinks
   iv. Coffee: Instant Cappucino
      1. Sugar 30-40%
      2. Milk Powder 24-35%
      3. Soluble Coffee 20-25%
      4. Lactose 1-15%
      5. Food Grade Emulsifier 1-3%
      6. Encapsulated Volatile Flavor 0.01-0.5%
   v. Tea
   vi. Alcoholic r) Spice blends and consumer prepared foods
   i. Powder gravy, sauce mixes
   ii. Condiments
   iii. Fermented Products s) Ready to heat foods: ready meals and soups, preferably selected from the group consisting of powdered soups, instant soups, precooked soups
   i. Soups
   ii. Sauces
   iii. Stews
   iv. Frozen entrees t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products Flavored milk beverages
   i. Yoghurt
   ii. Ice cream
   iii. Bean Curd
   iv. Cheese u) Soya protein or other soybean fractions, preferably selected from the group consisting of soya milk and products produced therefrom, soya lecithin-containing preparations, fermented products such as tofu or tempeh or products produced therefrom and soy sauces;

v) Meat products, preferably selected from the group consisting of ham, fresh or raw sausage preparations, and seasoned or marinated fresh or salt meat products w) Eggs or egg products, preferably selected from the group consisting of dried egg, egg white and egg yolk x) Oil-based products or emulsions thereof, preferably selected from the group consisting of mayonnaise, remoulade, dressings and seasoning preparations y) fruit preparations, preferably selected from the group consisting of jams, sorbets, fruit sauces and fruit fillings; vegetable preparations, preferably selected from the group consisting of ketchup, sauces, dried vegetables, deep-frozen vegetables, precooked vegetables, vegetables in vinegar and preserved vegetables z) Flavored pet foods.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

The terms "polyfunctional isocyanate," "multifunctional isocyanate," and "polyisocyanate" all refer to a compound having two or more isocyanate (—NCO) groups.

The terms "polyfunctional amine," "multifunctional amine," and "polyamine" refers to a compound containing two or more primary or secondary amine groups. These terms also refers to a compound containing one or more primary/secondary amine groups and one or more hydroxyl groups (—OH).

The terms "polyfunctional alcohol," "multifunctional alcohol," "poly alcohol," and "polyol" refer to a compound having two or more hydroxyl groups.

The invention is described in greater detail by the following non-limiting examples. Without further elaboration, it is believed that one skilled in the art can, based on the description herein, utilize the present invention to its fullest extent. All publications cited herein are incorporated by reference in their entirety.

EXAMPLE 1

Capsule 1 (BPEI and a Mixture of Polystyrene Sulfonate and CMC)

In a beaker, 96 grams ("g") of a fragrance accord (International Flavors and Fragrance, Union Beach, N.J.) was combined with 24 g of NEOBEE oil M-5 (caprylic/capric triglyceride, Stepan, Chicago, Ill.) and 9.6 g of isocyanate monomer, TAKENATE D110-N (trimethylol propane-adduct of xylylene diisocyanate, Mitsui Chemicals Corporation, Rye Brook, N.Y.), to form an oil phase. In a separate beaker, an aqueous solution (130 g) containing 1% of FLEXAN II (polystyrene sulfonate, Akzo Nobel, Bridgewater, N.J.) was mixed with an aqueous solution (30 g) of 1% carboxymethyl cellulose ("CMC", WALOCEL CRT 50000 PA 07, Dow, Midland, Mich.) to form an aqueous phase. The oil phase was then emulsified into the aqueous phase to form a fragrance emulsion under shearing (ULTRA TURRAX, T25 Basic, IKA WERKE) at 6500 rpm for two minutes.

To the fragrance emulsion was added 10.4 g of a 49% branched polyethylenimine aqueous solution ("BPEI", Sigma-Aldrich, St. Louis, Mo.) under constant mixing with an overhead mixer. Formation of capsules was immediately visible by optical microscopy. The mixer speed was reduced after the addition of branched polyethylenimine was complete. The capsule slurry was cured at 55° C. for two hours to obtain Capsule 1.

EXAMPLE 2

Capsule 2 (BPEI and a Mixture of PVP and PQ-11)

In a beaker, 96 g of a fragrance accord (International Flavors and Fragrance, Union Beach, N.J.) was combined with 24 g of NEOBEE oil M-5 and 9.6 g of TAKENATE D110-N to form an oil phase. In a separate beaker, an aqueous solution (130 g) containing 1.1% of PVP (polyvinylpyrrolidone, Luviskol® K 90 Pulver, BASF, Ludwigshafen, Germany) was mixed with an aqueous solution (30 g) of 20% POLYQUATERNIUM-11 (PQ11, Vinyl pyrrolidone/dimethylaminoethyl methacrylate copolymer, cationic polymer, LUVIQUAT PQ11 AT 1, Ludwigshafen, Germany) to form an aqueous phase. The oil phase was then emulsified into the aqueous phase to form a fragrance emulsion under shearing (ULTRA TURRAX, T25 Basic, IKA WERKE) at 9500 rpm for two minutes.

To the fragrance emulsion was added 10.4 g of a 49% BPEI aqueous solution under constant mixing with an overhead mixer. The mixer speed was reduced after the addition of crosslinker was complete. The capsule slurry was cured at 55° C. for two hours to obtain Capsule 2.

EXAMPLE 3

Capsule 3 (HMDA and a Mixture of PVP and PQ-11)

In a beaker, 96 g of a fragrance accord (International Flavors and Fragrance, Union Beach, N.J.) was combined with 24 g of Neobee oil and 9.6 g of isocyanate monomer, Lupranate®M20 (a polymeric methylene diphenyl diisocyanate commercially available from BASF corporation, Wyandotte, Mich., USA) to form an oil phase. In a separate beaker, an aqueous solution (160 g) containing 1% polyvinylpyrrolidone (Luviskol® K90, BASF, Ludwigshafen, Germany) and 4% polyquaternium-11 was used as an aqueous phase. The oil phase was then emulsified into the aqueous phase to form a fragrance emulsion under shearing (Ultra Turrax®, T25 Basic, IKA® WERKE) at 12500 rpm for two minutes.

The fragrance emulsion was heated to 35° C. in a round bottom vessel and to which 10.8 g of 40% hexamethylene diamine (HMDA) (INVISTA, Wichita, Kans., USA) was added under constant mixing with an overhead mixer. Formation of capsule was immediately visible by optical microscopy. The mixer speed was reduced after the addition of HMDA was complete. The capsule slurry was cured at 55° C. for two hours to obtain Capsule 3.

EXAMPLE 4

Capsule 4 (HMDA and a Mixture of Flexan II and CMC)

In a beaker, 96 g of a fragrance accord (International Flavors and Fragrance, Union Beach, N.J.) was combined with 24 g of Neobee oil and 9.6 g of Lupranate®M20 to form an oil phase. In a separate beaker, an aqueous solution (130 g) containing 1.0% of FLEXAN II was mixed with an aqueous solution (30 g) of 2% CMC to form an aqueous phase. The oil phase was then emulsified into the aqueous phase to form a fragrance emulsion under shearing (Ultra Turrax®, T25 Basic, IKA® WERKE) at 9500 rpm for two minutes.

The fragrance emulsion was heated to 35° C. in a round bottom vessel and to which 10.8 g of a 40% HMDA aqueous solution was added under constant mixing with an overhead mixer. Formation of capsule was immediately visible by optical microscopy. The mixer speed was reduced after the addition of HMDA was complete. The capsule slurry was cured at 55° C. for two hours to obtain Capsule 4.

EXAMPLE 5

Capsule 5 (A Mixture of Morwet D-425 and PVP)

In a beaker, 96 g of a fragrance accord (International Flavors and Fragrance, Union Beach, N.J.) was combined with 24 g of Neobee oil and 9.6 g of Lupranate®M20 to form an oil phase. In a separate beaker, an aqueous solution (160 g) containing 1% Morwet D-425 (a sodium salt of naphthalene sulfonate condensate commercially available from Akzo Nobel, Fort Worth, Tex., USA) and 1% polyvinylpyrrolidone (Luviskol®K90, BASF, Ludwigshafen, Germany) was used as an aqueous phase. The oil phase was then emulsified into the aqueous phase to form a fragrance emulsion under shearing (Ultra Turrax®, T25 Basic, IKA® WERKE) at 9500 rpm for two minutes.

The fragrance emulsion was heated to 35° C. in a round bottom vessel and to which 10.8 g of a 40% HMDA aqueous solution was added under constant mixing with an overhead mixer. Formation of capsule was immediately visible by optical microscopy. The mixer speed was reduced after the addition of HMDA was complete. The capsule slurry was cured at 55° C. for two hours to obtain Capsule 5.

EXAMPLE 6

Preparation of Composition A

A composition of this invention, i.e., Composition A, was prepared by mixing 264 g of Capsule 1, 6 g of a 10 wt % GELWHITE GP (a montmorillonite clay) water solution, and 30 g of a 5 wt % polyquaternium-11 water solution. The resultant mixture was stirred for 30 minutes via an overhead IKA lab mixer until the polymer solution was completely dissolved.

Two comparative compositions were also prepared, i.e., Comparatives A1' and A2'. Comparative A1' was prepared following exactly the same procedure as Composition 1 except that no polyquaternium-11 was used. Comparative A2' was also prepared following exactly the same procedure as Composition A except that no GELWHITE GP was used.

The composition stability was evaluated by aging the Composition A and Comparatives A1' and A2' at 45° C. over a period of 4 weeks. Capsule 1 was used as the control sample. Photographic pictures were taken to illustrate the stability of the samples. The results indicated that there was no separation seen for the Composition A, while Capsule 1, and Comparatives A1' and A2' each displayed significant separation, demonstrating the benefit of the combination of the negatively charged clay and polyquaternium-11.

EXAMPLES 7-9

Preparation of Compositions B1-B3

Three compositions of this invention were prepared by combining Capsule 1 with a negatively charged clay and a cationic polymer. The clay was added as a 10 wt % aqueous solution and the cationic polymer was added as a 5 wt % aqueous solution. Their levels were shown in Table 2 below.

Twenty comparative compositions, i.e., Comparatives B1'-B20', were also prepared by combining Capsule 1 with an adjuvant at a level shown in Table 2 below.

TABLE 2

| Sample | Adjuvant | Chemical name | Level Used |
|---|---|---|---|
| B1' | MERQUAT 2001 (Polyquaternium-47) | Acrylic acid/methacrylamidopropyl trimethyl ammonium chloride/methyl acrylate terpolymer, cationic polymer | 1% |
| B2' | LUVIQUAT PQ11 (Polyquaternium-11) | Vinyl pyrrolidone/dimethylaminoethyl methacrylate copolymer, cationic polymer | 1% |
| B3' | (Polyquaternium-4) | Hydroxyethyl cellulose dimethyl diallylammonium chloride copolymer | 0.5% |
| B4' | LUVISKOL K90 | Polyvinylpyrrolidone, a non-ionic polymer | 0.5% |
| B5' | LUVISKOL K30 | Polyvinylpyrrolidone, a non-ionic polymer | 0.5% |
| B6' | LUVISKOL K17 | Polyvinylpyrrolidone, a non-ionic polymer | 1% |
| B7' | LUVISKOL VA 73W | Vinylpyrrolidone/vinylacetate copolymer, non-ionic polymer | 0.5% |
| B8' | LUVISKOL Plus | Polyvinylcaprolactam, a non-ionic polymer | 0.5% |
| B9' | MOWIOL 18-88 | Polyvinyl Alcohol, a non-ionic polymer | 1% |
| B10' | PLURACARE F127 | Ethylene oxide/propylene oxide copolymer, a non-ionic polymer | 0.5% |
| B11' | SENSOMER 10M (Polyquaternium-10) | Polymeric quaternary ammonium derivative of hydroxyethyl cellulose, cationic polymer | 0.05% |
| B12' | SENSOMER JR 30M (Polyquaternium-10) | Polymeric quaternary ammonium derivative of hydroxyethyl cellulose, cationic polymer | 0.05% |
| B13' | UCARE JR 125 (Polyquaternium-10) | Polymeric quaternary ammonium derivative of hydroxyethyl cellulose, cationic polymer | 0.1% |
| B14' | UCARE JR 400 (Polyquaternium-10) | Polymeric quaternary ammonium derivative of hydroxyethyl cellulose, cationic polymer | 0.1% |

TABLE 2-continued

| Sample | Adjuvant | Chemical name | Level Used |
|---|---|---|---|
| B15' | SALCARE SC 96 (Polyquaternium-37) | Poly(2-methacryloxy-ethyltrimethylammonium chloride), cationic polymer | 0.02% |
| B16' | MERQUAT 550PR (Polyquaternium-7) | Poly(acrylamide-co-diallyldimethylammonium chloride), cationic polymer | 0.2% |
| B17' | MERQUAT 2200 (Polyquaternium-7) | Poly(acrylamide-co-diallyldimethylammonium chloride), cationic polymer | 0.2% |
| B18' | GELWHITE GP | a negatively charged clay | 0.2% |
| B19' | Xanthan Gum | A non-ionic polysaccharide | 0.1% |
| B20' | Sodium Carboxymethyl-cellulose (CMC) | An anionic cellulose | 0.1% |
| B1 | GELWHITE GP + polyquaternium-47 | | 0.2% + 0.5% |
| B2 | GELWHITE GP + polyquaternium-7 | | 0.2% + 0.5% |
| B3 | GELWHITE GP + polyquaternium-4 | | 0.2% + 0.5% |
| Capsule 1 | No Additive | No Additive | N/A |

Stability Evaluation

To evaluate the storage stability of Compositions B1-B3 and Comparatives B1'-B20', each sample was divided into 2 vials. One vail was placed at room temperature and the other at 45° C. The samples were periodically examined for creaming and gelling. The amount of separation was measured using a graduated cylinder after 4 weeks. Capsule 1 was used as a control. The results are given in Table 3 below.

The results show that Compositions B1-B2 each have a good stability when storing at room temperature and at 45° C. The viscosity of Compositions B1-B2 was measured by Brookfield DV-111 Ultra Programmable viscometer (Brookfield Engineering Laboratories, Inc., Middleboro, Mass., USA). The results are presented in Table 4 below.

TABLE 3

| Sample | Room Temp., 4 weeks | 45° C., 4 weeks |
|---|---|---|
| B1' | Not flowable, 6% water separation at bottom | Not flowable. 8% water separation at bottom |
| B2' | Not flowable, 10% water separation at bottom | Not flowable. 9% water separation at bottom |
| B3' | Flowable, 8% water separation | Not flowable, 13% water separation |
| B4' | Not flowable, 25% water separation | Not flowable, 24% water separation |
| B5' | Not flowable, 25% water separation | Not flowable, 24% water separation |
| B6' | Not flowable, 20% water separation | Not flowable, 22% water separation |
| B7' | Not flowable, 25% water separation | Not flowable, 20% water separation |
| B8' | Not flowable, 13% water separation | Not flowable, 18% water separation |
| B9' | Not flowable, 15% water separation | Not flowable, 12% water separation |
| B10' | Not flowable, 25% water separation | Not flowable, 23% water separation |
| B11' | Not flowable, 25% water separation | Not flowable, 25% water separation |
| B12' | Not flowable, 23% water separation | Not flowable, 20% water separation |
| B13' | Not flowable, 25% water separation | Not flowable, 27% water separation |
| B14' | Not flowable, 20% water separation | Not flowable, 17% water separation |
| B15' | Not flowable, 25% water separation | Not flowable, 27% water separation |
| B16' | Not flowable, 5% water separation | Not flowable, 2% water separation |
| B17' | Not flowable, 25% water separation | Not flowable, 26% water separation |
| B18' | Not flowable, 26% water separation | Not flowable, 25% water separation |
| B19' | Not flowable, 17% water separation | Not flowable, 19% water separation |
| B20' | Flowable, 6% water separation | Not flowable, cake on top, 6% water separation |
| B1 | Flowable, 15.5% water separation | Flowable, 17.8% water separation |
| B2 | Flowable, 20% water separation | Flowable, 18.6% water separation |
| B3 | Flowable, no water separation | Flowable, no water separation |
| Capsule 1 | Flowable, 10% water separation | Not flowable, 9% water separation |

Each comparative composition had a viscosity of greater than 6666 cP (the detection limitation of the instrument) after storing at 45° C. for 4 weeks.

TABLE 4

| Sample | Viscosity (cP) Room Temp., 4 weeks |
|---|---|
| B1 | 2370 |
| B2 | 913.3 |
| Capsule 1 | >6666 |

EXAMPLES 10-12

Five more microcapsule compositions of this invention, i.e., Compositions C1-C5, were prepared using Capsule 1 by following the procedure described in Examples 7-9 above. Comparative Compositions C1', C2', and C3' were also prepared. The levels of the cationic polymer (PQ-4 or PQ-47) and Gelwhite GP were shown in Table 6 below. The viscosity of each sample was measured after storing at room temperature for 4 weeks (See Table 5).

TABLE 5

| Composition | Level used | Viscosity (cP) Room Temp., 4 weeks |
|---|---|---|
| Capsule 1 | | >6666 |
| Comparative C1': Gelwhite only | 0.2% | >6666 |
| Comparative C2': PQ-4 only | 0.5% | 2293 |
| Composition C1: Gelwhite + PQ-4 | 0.2% + 0.5% | 913.3 |
| Composition C2: Gelwhite + PQ-4 | 0.2% + 0.25% | 1733 |
| Composition C3: Gelwhite + PQ-4 | 0.1% + 0.5% | 1370 |
| Comparative C3': PQ47 only | 0.5% | >6666 |
| Composition C4: Gelwhite + PQ47 | 0.2% + 0.5% | 2147 |
| Composition C5: Gelwhite + PQ47 | 0.2% + 0.25% | 2620 |

Three additional microcapsule compositions of this invention, i.e., Compositions D1-D3, were prepared using Capsule 5 described in Example 5, together with PQ-4 and Gelwhite. The procedure described in Examples 7-9 was followed. Comparative Compositions D1' and D2' were also prepared. The levels of the cationic polymer (PQ-4) and Gelwhite GP were shown in Table 6 below. The viscosity of each sample was measured after storing at room temperature for 4 weeks (See Table 6).

TABLE 6

| Composition | Concentration used | Viscosity (cP) (Room Temp., 4 weeks) |
|---|---|---|
| Capsule 5 | 0% | >6666 |
| Comparative D1': Gel white only | 0.2% | >6666 |
| Comparative D2': PQ-4 only | 0.5% | >6666 |
| Composition D1: Gelwhite + PQ-4 | 0.2% + 0.5% | 1327 |
| Composition D2: Gelwhite + PQ-4 | 0.2% + 0.25% | 2820 |
| Composition D3: Gelwhite + PQ-4 | 0.1% + 0.5% | 2560 |

EXAMPLE 13

Sensory Performance of Stabilized Capsule Formulation

The sensory performance of adjuvant-stabilized polyurea capsule formulations in a roll-on base was evaluated. The roll on formulation is shown in Table 7.

TABLE 7

| Ingredient | Amount |
|---|---|
| Water | to 100% |
| Aluminum Chlorohydrate or Aluminum Zirconium Tetrachlrohydrex Gly | 32-36% |
| Steareth-2, Stearth-20 | 0.5-4% |
| Capsule 1 | 1-5% |
| Glycerin | 3-5% |
| Dimethicone | 0.5 |

Panelists (30-35, with a mix of male and female) were instructed to shower with an unfragranced soap on the day of evaluation. For the comparative analysis, one underarm was applied with the test sample, the other with a control sample. The samples were composed of 0.35 g of roll-on base, pre-measured in a plastic syringe for easy application onto skin. Application of the samples was counterbalanced across underarms. Fragrance intensity was evaluated at 0, 8, 12 and 24 hours after application on a 0-10 intensity scale. Intensity ratings were entered by panelists into an automated data entry system, (COMPUSENSE at-hand) at the designated times. Intensity scores were averaged across panelists for each sample and analyzed by Two-Way ANOVA ($p<0.1$/90% CI).

EXAMPLE 14

Clear Deodorant Stick Formulation

An exemplary clear deodorant stick formulation is provided in Table 8.

TABLE 8

| Ingredient | Percentage |
|---|---|
| Water | 20 |
| Phosphatidylglycerol/Diphosphatidylglycerol | 55 |
| Sodium Stearate | 6 |
| PEG-4 | 15 |
| Antibacterial Agent | 0.1 |

EXAMPLE 15

Antiperspirant Emulsion Spray Formulation

An exemplary antiperspirant emulsion spray formulation is provided in Table 9.

TABLE 9

| Ingredient | Percentage |
| --- | --- |
| Water | to 100 |
| Dimethicone | 6 |
| Aluminum Chlorohydrate | 5-6 |
| EDTA | 0.15 |
| Lauryl PEG-9 Polydimethylsiloxyethyl Dimethicone | 0.3 |
| Phenoxyethanol | 0.3 |
| Isobutane | 70 |

EXAMPLE 16

Antiperspirant Emulsion Roll-On Formulation

An exemplary antiperspirant emulsion roll-on formulation is provided in Table 10.

TABLE 10

| Ingredient | Percentage |
| --- | --- |
| Water | to 100 |
| Aluminum Chlorohydrate or Aluminum Zirconium Tetrachlorohydrex Gly | 32-36 |
| Steareth-2, Steareth-20 | 0.5-4 |
| Polyurea | 1-5 |
| Glycerin | 3-5 |
| Dimethicone | 0.5 |

EXAMPLE 17

Antiperspirant Clear Emulsion Stick Formulation

An exemplary antiperspirant clear emulsion stick formulation is provided in Table 11.

TABLE 11

| Ingredient | Percentage |
| --- | --- |
| Water | 40 |
| Aluminum Zirconium Tetrachlorohydrex Gly | 20 |
| Stearyl Alcohol | 30 |
| C12-C15 Alkyl Benzoate | 25 |
| Glycine | 7 |
| Dimethicone | 0.07 |

EXAMPLE 18

Antiperspirant Opaque Emulsion Stick Formulation

An exemplary antiperspirant opaque emulsion stick formulation is provided in below Table 12.

TABLE 12

| Ingredient | Percentage |
| --- | --- |
| Water | to 100 |
| Aluminum Chlorohydrate | 40 |
| Isopropyl Palmitate | 9 |
| Dimethicone | 5.8 |
| Synthetic Wax | 9 |
| Beheneth-10 | 2 |
| Polyglyceryl-3 Diisosterate | 0.3 |
| Acrylates Copolymer | 0.3 |
| PEG/PPG-18/18 Dimethicone | 2 |
| Phenoxyethanol | 0.5 |
| Pentylene Glycol | 0.5 |
| Cetyl PEG/PPG-10/1 Dimethicone | 2 |

EXAMPLE 19

Deodorant Spray Formulation

An exemplary deodorant spray formulation is provided in Table 13.

TABLE 13

| Ingredient | Percentage |
| --- | --- |
| Denatured Alcohol | 45 |
| Polyaminopropyl biguanide stearate | 0.2-0.5 |
| Butane, Isobutane, Propane, 152A | 55 |

EXAMPLE 20

Antiperspirant Clear Gel Formulation

An exemplary antiperspirant clear gel formulation is provided in Table 14.

TABLE 14

| Ingredient | Percentage |
| --- | --- |
| Water | 20 |
| Aluminum Zirconium Tetrachlorohydrex Gly | 25 |
| Silicone | 40 |
| Phosphatidylglycerol | 10 |
| Emulsifier | 10 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of preparing a stable microcapsule composition, one skilled in the art can choose a capsule, clay, and cationic polymer. Further, the ratios among the capsule, clay, and cationic polymer can also be determined by a skilled artisan without undue experimentation.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A stable microcapsule composition comprising a microcapsule dispersed in an aqueous phase and a stabilizing agent, wherein the stabilizing agent is a combination of a negatively charged clay and a cationic polymer, the microcapsule is a core-shell microcapsule having a microcapsule wall and a microcapsule core encapsulated by the microcapsule wall, and the cationic polyquaternium polymer is a hydroxyethyl cellulose dimethyl diallylammonium chloride copolymer (PQ-4).

2. The stable microcapsule composition of claim 1, wherein the microcapsule is present at a level of 20 to 70% by weight.

3. The stable microcapsule composition of claim 1, wherein the negatively charged clay is present at a level of 0.05 to 2%, preferably 0.05 to 1%, and more preferably 0.1 to 0.5%; and the cationic polymer is present at a level of 0.05 to 5%, preferably 0.1 to 2%, and more preferably 0.2 to 0.7%.

4. The stable microcapsule composition of claim 1, wherein the negatively charged clay is a montmorillonite clay.

5. The stable microcapsule composition of claim 1, wherein the microcapsule is a core-shell microcapsule having a microcapsule wall and a microcapsule core encapsulated by the microcapsule wall: the microcapsule wall is formed of an encapsulating polymer selected from the group consisting of a polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), and combination thereof; and the microcapsule core contains an active material selected from the group consisting of a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, and combination thereof.

6. The stable microcapsule composition of claim 1, wherein the composition has a pH value of 4 to 8.

7. The stable microcapsule composition of claim 5, further comprising an alkylnaphthalenesulfonate formaldehyde condensate, polyvinylpyrrolidone, polyvinyl alcohol, polystyrene sulfonate, carboxymethyl cellulose, sodium salt of naphthalene sulfonate condensate, copolymer of vinyl pyrrolidone and quaternized dimethylaminoethyl methacrylate, or a combination thereof; wherein the encapsulating polymer is a polyurea, polyurethane, or a combination thereof; the polyurea is a reaction product of a polyfunctional isocyanate and a polyfunctional amine; and the polyurethane is a reaction product of a polyfunctional isocyanate and a polyfunctional alcohol as a cross-linking agent.

8. The stable microcapsule composition of claim 7, wherein the polyfunctional isocyanate is an aromatic polyfunctional isocyanate, aliphatic polyfunctional isocyanate, or combination thereof; the aromatic polyfunctional isocyanate contains a phenyl, tolyl, xylyl, naphthyl, diphenyl moiety, or a combination thereof; and the aliphatic polyfunctional isocyanate is a trimer of hexamethylene diisocyanate, a trimer of isophorone diisocyanate, a biuret of hexamethylene diisocyanate, or a combination thereof.

9. The stable microcapsule composition of claim 8, wherein the aromatic polyfunctional isocyanate is selected from the group consisting of polymeric methylene diphenyl diisocyanate, polyisocyanurates of toluene diisocyanate, trimethylol propane-adducts of toluene diisocyanate, trimethylol propane-adducts of xylylene diisocyanate, and combinations thereof; and the aliphatic polyfunctional isocyanate is selected from the group consisting of dimers, biurets, symmetric trimers, asymmetric trimers of hexamethylene diisocyanate, and combinations thereof.

10. The stable microcapsule composition of claim 7, wherein the polyfunctional amine is hexamethylene diamine, hexaethylenediamine, ethylenediamine, 1,3-diaminopropane, 1,4-diamino-butane, diethylenetriamine, pentaethylenehexamine, 1,6-diaminohexane, hydrazine, 1,4-diaminocyclohexane, 1,3-diamino-l-methylpropane, bis(3-aminopropyl)amine, bis(hexanethylene)triamine, tris(2-aminoethyl)amine, triethylene-tetramine, N,N'-bis(3-aminopropyl)-1,3-propanediamine, tetraethylenepentamine, branched polyethylenimine, chitosan, nisin, gelatin, 1,3-diamino-guanidine, 1,1-dimethylbiguanide, guanidine, arginine, lysine, ornithine, histidine, amino-2-methyl-1-propanol, or a combination thereof.

11. The stable microcapsule composition of claim 7, wherein the microcapsule composition contains the alkylnaphthalenesulfonate formaldehyde condensate and polyvinylpyrrolidone, each of which, independently, is present at a level of 0.1 to 5% by weight of the microcapsule composition, and the ratio between the alkylnaphthalenesulfonate formaldehyde condensate and polyvinylpyrrolidone is 10:1 to 1:10.

12. The stable microcapsule composition of claim 11, wherein the encapsulating polymer is a polyurea that is a reaction product of a polyfunctional isocyanate and a polyfunctional amine, the polyfunctional isocyanate contains a trimethylol propane-adduct of toluene diisocyanate or a trimethylol propane-adduct of xylylene diisocyanate, and the polyfunctional amine is diethylenetriamine, bis(3-aminopropyl)amine, bis(hexanethylene)triamine, tris(2-aminoethyl)amine, triethylenetetramine, N,N'-bis(3-aminopropyl)-1,3-propanediamine, tetraethylenepentamine, pentaethylenehexamine, branched polyethylenimine, chitosan, nisin, gelatin, 1,3-diaminoguanidine monohydrochloride, 1,1-dimethylbiguanide hydrochloride, or guanidine carbonate, or mixture thereof.

13. The stable microcapsule composition of claim 12, the composition further comprising a polyvinyl alcohol, polystyrene sulfonate, carboxymethyl cellulose, polyvinylpyrrolidone, sodium salt of naphthalene sulfonate condensate, copolymer of vinyl pyrrolidone and quaternized dimethylaminoethyl methacrylate, or combination thereof.

14. The stable microcapsule composition of claim 1, the composition further comprising a deposition aid selected from the group consisting of polyquaternium-5, polyquaternium-6, polyquaternium-7, polyquaternium-10, polyquaternium-16, polyquaternium-22, polyquaternium-24, polyquaternium-28, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, and combinations thereof.

15. The stable microcapsule composition of claim 1, the composition further comprising one or more free fragrances or one or more additional microcapsules.

16. A consumer product comprising a stable microcapsule composition of claim 1.

17. The consumer product of claim 16, wherein the consumer product is a shampoo, a hair conditioner, a hair rinse, a hair refresher, a hair fixative or styling aid, a hair bleach, a hair dye or colorant, a soap, a body wash, a cosmetic preparation, an all-purpose cleaner, a bathroom cleaner, a floor cleaner, a window cleaner, a bath tissue, a paper towel, a disposable wipe, a diaper rash cream or balm, a baby powder, a diaper, a bib, a baby wipe, an oral care product, a tooth paste, an oral rinse, an tooth whitener, a denture adhesive, a chewing gum, a breath freshener, an orally dissolvable strip, a chewable candy, a hard candy, a hand sanitizer, an anti-inflammatory balm, an anti-inflammatory ointment, an anti-inflammatory spray, a health care device, a dental floss, a toothbrush, a tampon, a feminine napkin, a personal care product, a sunscreen lotion, a sunscreen spray, a wax-based deodorant, a glycol type deodorant, a soap type deodorant, a facial lotion, a body lotion, a hand lotion, a body powder, a shave cream, a bath soak, an exfoliating scrub, a foot cream, a facial tissue, a cleansing wipe, a fabric care product, a fabric softener, a fabric refresher, an ironing water, a liquid laundry detergent, a liquid dish detergent, an automatic dish detergent, a unit dose tablet or capsule, a scent booster, a drier sheet, a fine fragrance, a solid perfume, a powder foundation, a liquid foundation, an eye shadow, a lipstick or lip balm, an Eau De Toilette product, a deodorant, a rug deodorizer, a candle, a room deodorizer, a disinfectant, an aerosol antiperspirant, a stick antiperspirant, a roll-on antiperspirant, an emulsion spray antiperspirant, a clear emulsion stick antiperspirant, a soft solid antiperspirant, an emulsion roll-on antiperspirant, a clear emulsion stick antiperspirant, an opaque emulsion stick antiperspirant, a clear gel antiperspirant, a clear stick deodorant, a spray deodorant, a baked product, a bread, a dry biscuit, a cake, a cookie, a chip, a popcorn, a pretzel, an extruded snack, a breakfast cereal, a muesli bar, a precooked finished rice product, an alcoholic or non-alcoholic beverage, a spice blend, a soup, a sauce, a stew, a frozen entree, a yogurt, an ice cream, a bean curd, a cheese, a soya protein product, a meat product, an egg product, a mayonnaise, a remoulade, a dressing, a seasoning preparation, a fruit preparation, or a vegetable preparation.

\* \* \* \* \*